United States Patent
Kwok et al.

(10) Patent No.: US 11,478,154 B2
(45) Date of Patent: Oct. 25, 2022

(54) TESTING DEVICE FOR NON-INVASIVE PHYSIOLOGICAL INFORMATION DETECTING DEVICE AND METHOD THEREOF

(71) Applicant: BELUN TECHNOLOGY (IP) COMPANY LIMITED, Shatin (HK)

(72) Inventors: Ka Cheung Kwok, Shatin (HK); Ngok Man Sze, Shatin (HK); Luis Ng, Shatin (HK); Kwan Wai To, Shatin (HK)

(73) Assignee: BELUN Technology (IP) Company Limited, Shatin (HK)

( * ) Notice: Subject to any disclaimer, the term of this patent is extended or adjusted under 35 U.S.C. 154(b) by 237 days.

(21) Appl. No.: 16/650,789

(22) PCT Filed: Sep. 25, 2018

(86) PCT No.: PCT/CN2018/107339
§ 371 (c)(1),
(2) Date: Mar. 25, 2020

(87) PCT Pub. No.: WO2019/057204
PCT Pub. Date: Mar. 28, 2019

(65) Prior Publication Data
US 2020/0237236 A1    Jul. 30, 2020

Related U.S. Application Data

(60) Provisional application No. 62/562,512, filed on Sep. 25, 2017.

(30) Foreign Application Priority Data

Nov. 14, 2017   (CN) .......................... 201711124485.5

(51) Int. Cl.
*A61B 5/02* (2006.01)
*G01N 21/55* (2014.01)
*A61B 5/1455* (2006.01)

(52) U.S. Cl.
CPC ......... *A61B 5/02007* (2013.01); *G01N 21/55* (2013.01); *A61B 5/14551* (2013.01)

(58) Field of Classification Search
CPC ............ A61B 5/14532; A61B 5/14551; A61B 5/1455; A61B 8/06; A61B 5/0261;
(Continued)

(56) References Cited

U.S. PATENT DOCUMENTS 5,134,284 A * 7/1992 Volgyesi .............. G01N 21/278
250/252.1
5,166,517 A * 11/1992 Volgyesi ............ G01N 33/0006
250/252.1
(Continued)

FOREIGN PATENT DOCUMENTS

CN    1542521 A    11/2004
CN    1836632 A     9/2006
(Continued)

OTHER PUBLICATIONS

International Search Report dated Jan. 8, 2019 in counterpart PCT application PCT/CN2018/107339, 5 pages.
(Continued)

*Primary Examiner* — Michael P Stafira
(74) *Attorney, Agent, or Firm* — Juan Carlos A. Marquez; Marquez IP Law Office PLLC

(57) ABSTRACT

A testing device and method thereof verifies performance of a non-invasive physiological information detecting device. The testing device incorporates a first layer to modulate one or more electromagnetic signals, e.g., light, emitted from the non-invasive physiological information detecting device in a
(Continued)

first predetermined manner and a second layer to process the electromagnetic signal from the first layer such that the modulated signal received at the physiological information detecting device simulates a change in the electromagnetic signal during a real detecting process. In one embodiment, the second layer modulates one or more electromagnetic signals from the first layer in a second predetermined manner, wherein at least one of the first and second layers modulates one kind of the electromagnetic signals. In another embodiment, the first layer scatters different kinds of electromagnetic signals with different scattering ratios, and the second layer absorbs the electromagnetic signals passing through the first layer.

15 Claims, 14 Drawing Sheets

(58) Field of Classification Search
CPC .............. A61B 5/6826; A61B 5/02416; A61B 2562/0238; A61B 5/445; A61B 3/1241; A61B 5/021; A61B 5/14542; A61B 5/026; A61B 5/029; A61B 2562/0233; A61B 5/024; A61B 5/02433; A61B 8/02; A61B 8/065; A61B 2017/00057; A61B 5/0833; A61B 5/6876; A61B 5/0205; A61B 5/1495; A61B 5/02007; A61B 5/0086; G01N 2021/3144; G01N 21/31; G01N 21/49; G01N 2021/3155; G01N 2201/0221; G01N 2201/0627; G01N 21/3151; G01N 21/4795; G01N 2021/3137; G01N 21/359; G01N 21/474; G01N 2021/3148; G01N 21/274; G01N 33/54366; G01N 2021/0342; G01N 2021/1789; G01N 21/276; G01N 21/314; G01N 21/35; G01N 21/3581; G01N 21/55; G01N 21/78; G01N 2201/066; G01N 2201/0696; G01N 2201/08; G01N 33/4925; G01N 2021/399; G01N 2021/6432; G01N 21/1717; G01N 21/278; G01N 21/6408; G01N 21/6456; G01N 2201/084; G01N 2201/127; G01N 2021/7773; G01N 21/783; G01N 2201/0231; G01N 2201/062; G01N 2201/1211; G01N 33/84; G01N 35/00732; G01N 2021/3181; G01N 21/1702; G01N 2291/021; G01N 29/024; G01N 29/032; G01N 29/2418; G01N 33/0006; G01N 2021/3159; G01N 2021/4797; G01N 21/255; G01N 21/27; G01N 21/3577; G01N 21/4785; G01N 2201/0675; G01N 2201/0683; G01N 2201/0893; G01N 2201/1244; G01N 33/48; G01N 33/5302
See application file for complete search history.

(56) References Cited

U.S. PATENT DOCUMENTS

| | | | | |
|---|---|---|---|---|
| 5,278,627 | A * | 1/1994 | Aoyagi | G01N 21/274 250/252.1 |
| 6,400,973 | B1 * | 6/2002 | Winter | A61B 5/1495 600/323 |
| 7,389,029 | B2 * | 6/2008 | Rahman | B82Y 30/00 385/129 |
| 2006/0247507 | A1 * | 11/2006 | Ruiter | A61B 5/1495 600/331 |
| 2014/0275890 | A1 * | 9/2014 | Meehan | A61B 5/0002 600/324 |
| 2019/0261901 | A1 * | 8/2019 | Pologe | G01N 33/4925 |

FOREIGN PATENT DOCUMENTS

| | | | | |
|---|---|---|---|---|
| CN | 1864629 | A | | 11/2006 |
| CN | 100386054 | C | | 5/2008 |
| CN | 100386054 | C | * | 5/2008 |
| CN | 102389314 | A | | 3/2012 |
| CN | 103271745 | A | * | 9/2013 |
| CN | 103815917 | A | | 5/2014 |
| CN | 103271745 | B | | 5/2015 |
| CN | 204394524 | U | | 6/2015 |
| CN | 103876748 | B | | 12/2015 |
| CN | 108095733 | A | | 6/2018 |
| CU | 203388866 | U | | 1/2014 |
| JP | H067827 | B2 | | 2/1994 |
| WO | WO-2011033628 | A1 | * | 3/2011 .......... A61B 5/14552 |
| WO | WO-2011104888 | A1 | * | 9/2011 .......... A61B 5/14552 |
| WO | WO-2015174163 | A1 | * | 11/2015 .............. A61B 5/00 |

OTHER PUBLICATIONS

International Standard ISO 80601-2-61:2011 (E), dated Apr. 1, 2011, 92 pages.
"Evaluation of a Pulse Oximeter Sensor Tester," Hudzovic et al., International Journal of Clinical Monitoring and Computing (May 2011), 9 pages.

* cited by examiner

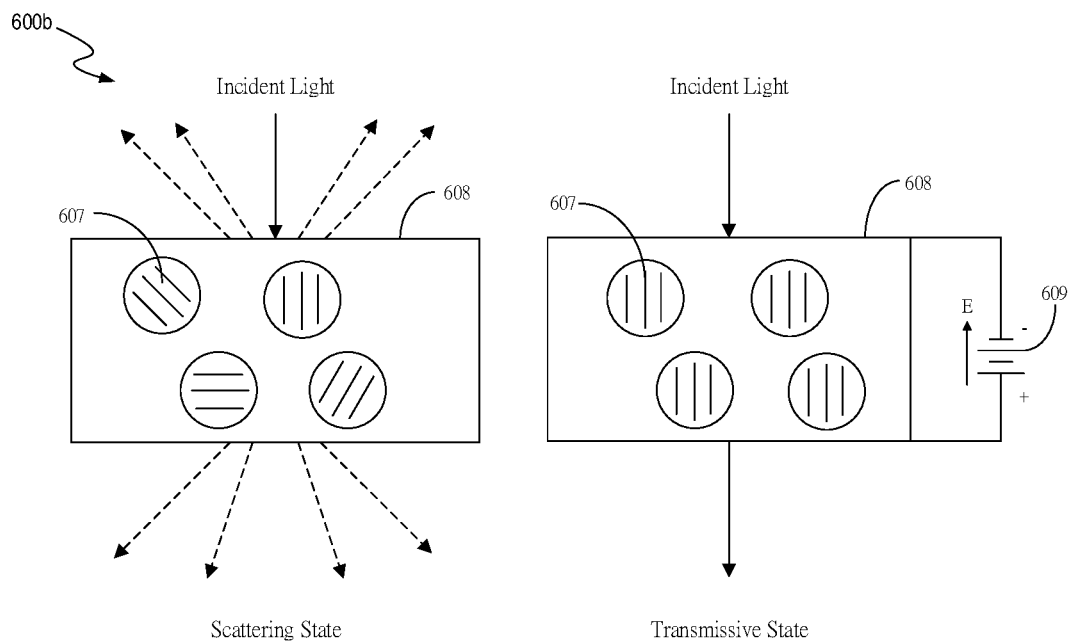
Figure 6B
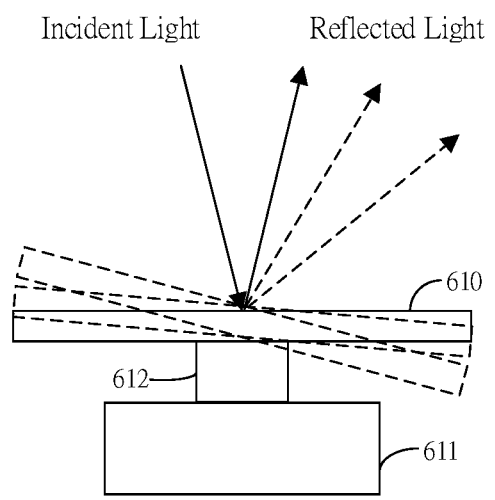
Figure 6C

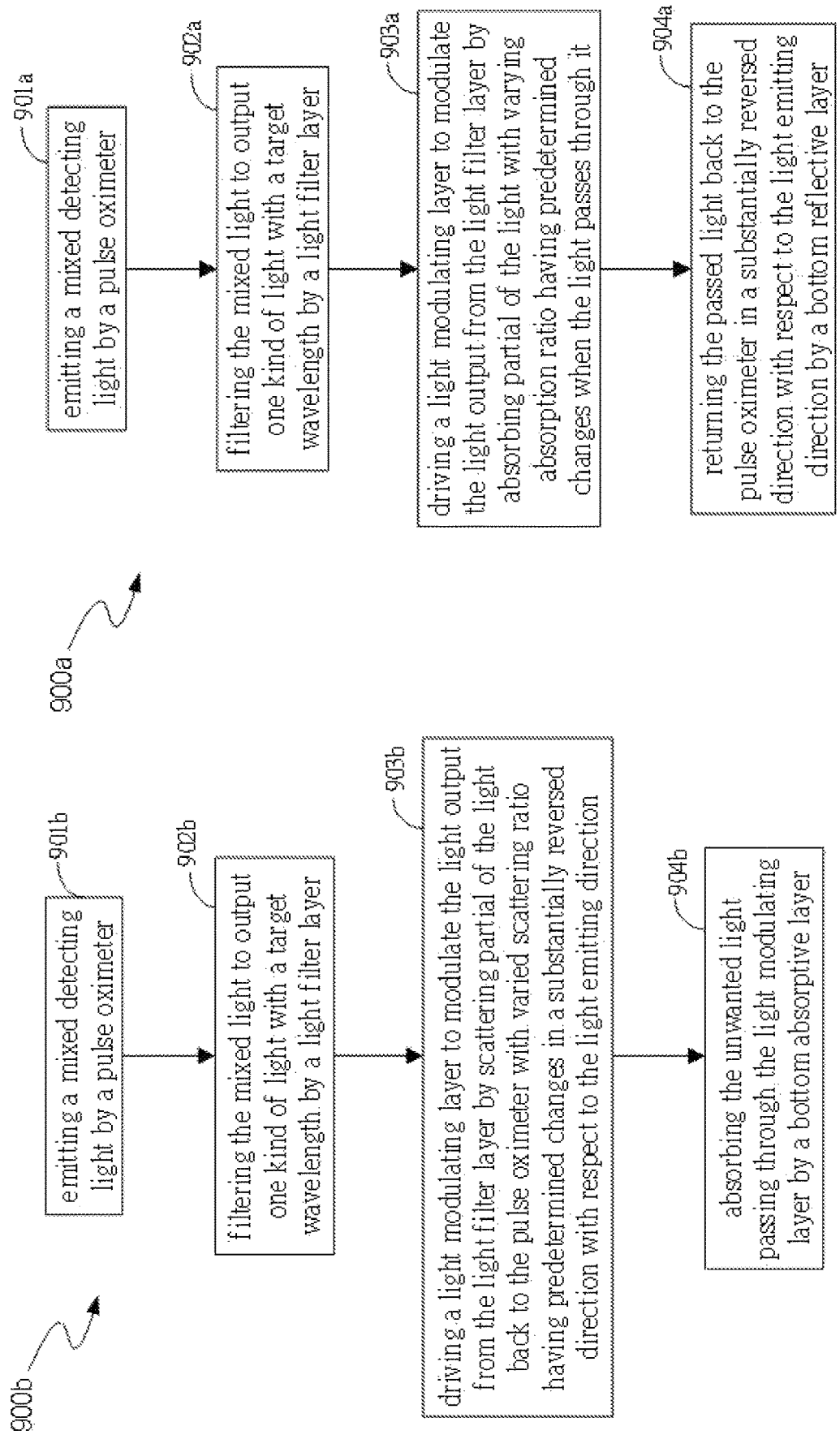

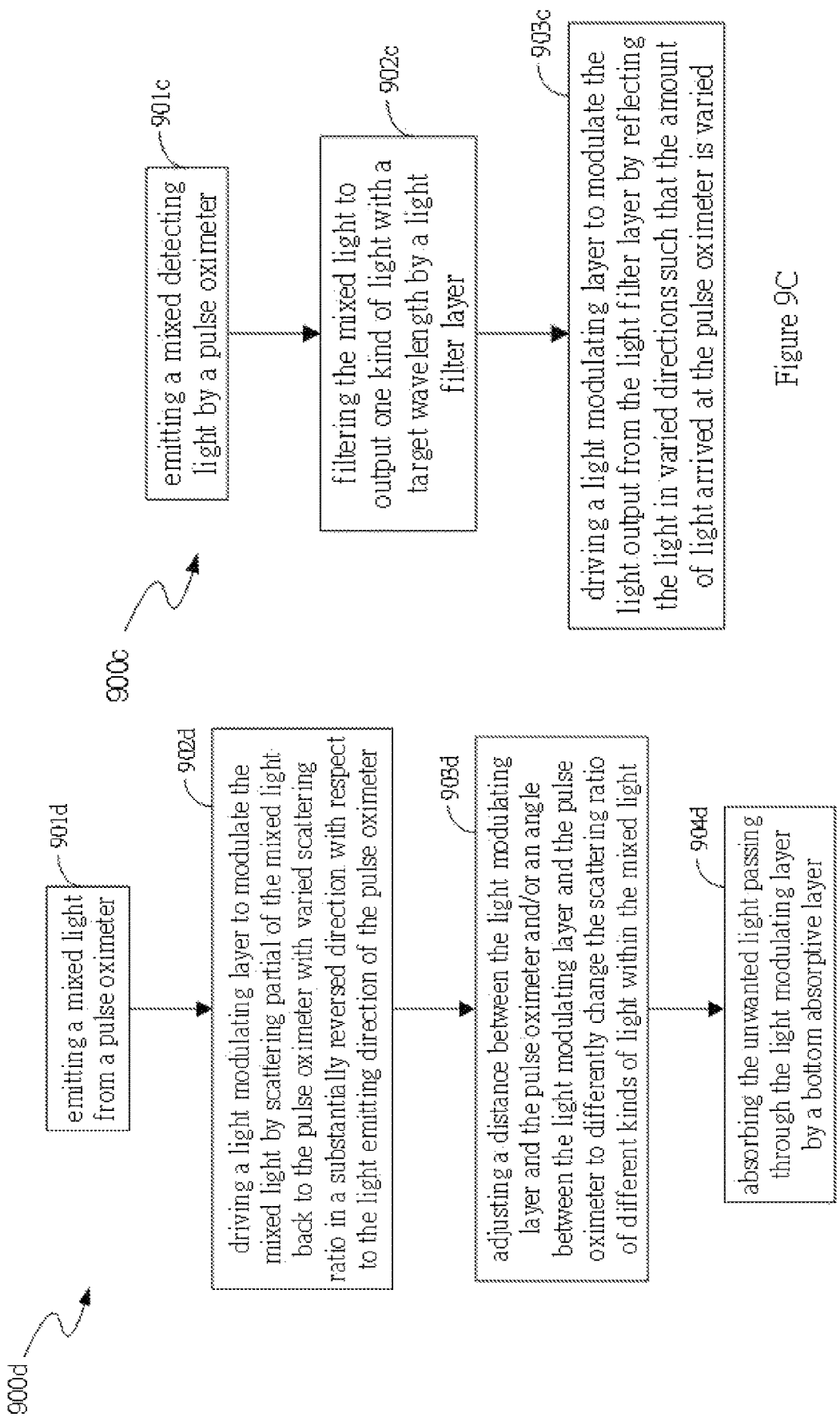

TESTING DEVICE FOR NON-INVASIVE PHYSIOLOGICAL INFORMATION DETECTING DEVICE AND METHOD THEREOF

PRIORITY RELATED APPLICATION

This application is the US national stage of PCT Application No. PCT/CN2018/107339 filed on Sep. 25, 2018, which is based on and claims priority to U.S. Patent Application No. 62/562,512, filed before the United States Patent and Trademark Office on Sep. 25, 2017 and entitled "A Testing Device for Pulse Oximetry and Method Thereof", the entire contents of which are incorporated herein by reference.

TECHNICAL FIELD

This invention relates to a device configured to be used in testing a healthcare device and more particularly, to a device for verifying the performance of a non-invasive physiological information detecting device and method thereof.

BACKGROUND

Nowadays, technology integrated with multiple health tools is a becoming a very popular trend within the healthcare industry and is increasingly being used on a more regular basis. Many of the wearable devices are providing a plethora of health data that can be used to inform both personal and clinical decisions for consumers utilize the growing roster of available tools, wherein the wearable pulse oximetry operable for measuring the pulse rate and/or blood oxygen saturation (SpO2) in a non-invasive way is becoming more and more important and popular to keep monitor the health status of the user.

A pulse oximeter is a sensing device for non-invasive measurement of a person's arterial-blood oxygen saturation level. The measurement is done by measuring absorbance of light beams with different kinds of pre-determined wavelength after the light beams travel through or are reflected by a pre-determined part of the person's body. Hereinafter, a light beam directed to the pre-determined part of the body for absorbance measurement is referred to as a probe light beam. For a transmissive oximeter, the probe light beams are usually directed to one side of a thin section of the body such as a finger, a palm or an earlobe, and light sensors are used to measure intensities of the light beams that pass through and exit this thin section from the opposite side. For a reflective oximeter, the probe light beams may be directed to the skin of a foot, forehead or chest, and light sensors are used to detect the light beams reflected from the incident skin. Typically, two pre-determined wavelengths respectively within a visible light range and an infra-red light range are used for the probe light beams of the pulse oximeter.

Generally, before the product of pulse oximetry leave the factory for sale or use, it is needed to verify the performance and test the functions of the products as manufacture design. If the pulse oximeter cannot pass the verification/test, it may be required to return factory repair, due to the malfunction of pulse oximeter monitor or electrical integrity of pulse oximeter probe, etc.

There is a need in the art for a testing device having a simple structure realized by minimal components to accurately verify the performance and test the functions of the pulse oximetry.

SUMMARY

One example embodiment is a testing device for verifying performance of a non-invasive physiological information detecting device. The testing device includes a first signal modulating layer being operable for receiving and modulating one or more electromagnetic signals from the physiological information detecting device; and a second signal modulating layer for receiving and modulating one or more electromagnetic signals from the first signal modulating layer, wherein at least one of the first and second signal modulating layers modulates one electromagnetic signal within the one or more electromagnetic signals.

BRIEF DESCRIPTION OF THE DRAWINGS

FIG. 6B illustrates another liquid crystal panel 600b being operable for light modulation, in accordance with another embodiment of the invention.

FIG. 6C illustrates a digital mirror device 600c being operable for light modulation, in accordance with one embodiment of the invention.

FIG. 9A illustrates a light modulating method 900a used for verifying the measurement performance of a non-invasive physiological information detecting device, in accordance with one embodiment of the presented invention.

FIG. 9B illustrates another light modulating method 900b used for verifying the measurement performance of a non-invasive physiological information detecting device, in accordance with another embodiment of the presented invention.

FIG. 9C illustrates another light modulating method 900c used for verifying the measurement performance of a non-invasive physiological information detecting device, in accordance with another embodiment of the presented invention.

FIG. 9D illustrates another light modulating method 900d used for verifying the measurement performance of a non-invasive physiological information detecting device, in accordance with another embodiment of the presented invention.

DETAILED DESCRIPTION

Figure 1:
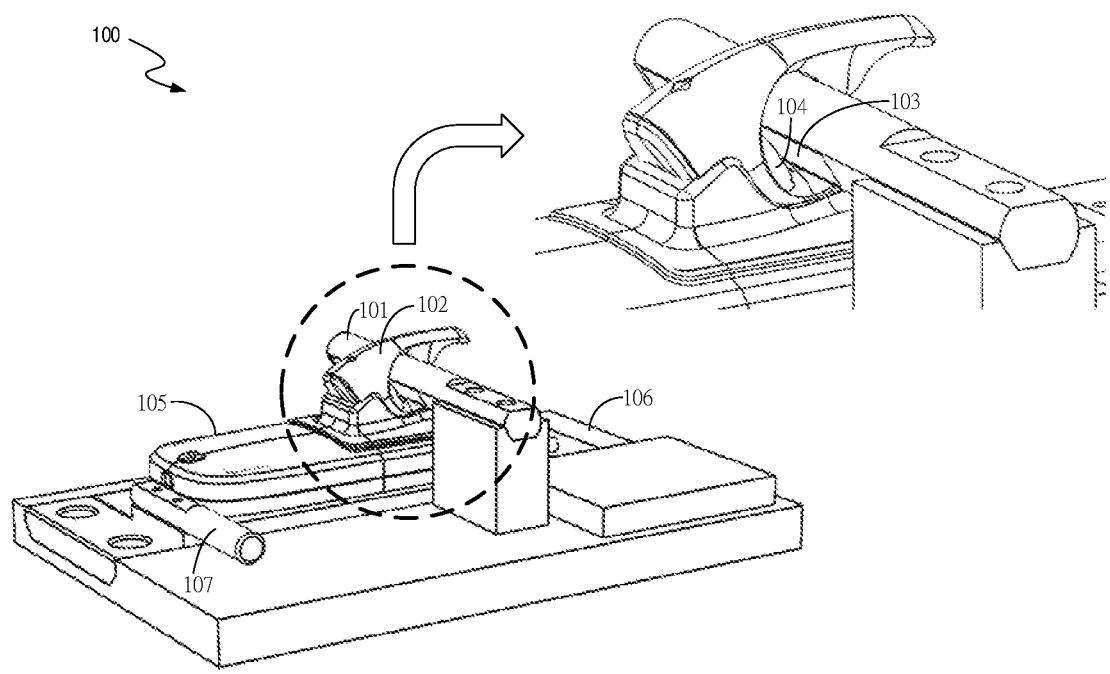
FIG. 1 shows an exemplary drawing of a testing device 100 being operable to verify the performance of a non-invasive physiological information detecting device, in accordance with one exemplary embodiment of the invention.

Reference will now be made in detail to the embodiments of the present invention. While the invention will be described in conjunction with these embodiments, it will be understood that they are not intended to limit the invention to these embodiments. On the contrary, the invention is intended to cover alternatives, modifications and equivalents, which may be included within the spirit and scope of the invention as defined by the appended claims.

Furthermore, in the following detailed description of the present invention, numerous specific details are set forth in order to provide a thorough understanding of the present invention. However, it will be recognized by one of ordinary skill in the art that the present invention may be practiced without these specific details. In other instances, well known methods, procedures, components, and circuits have not been described in detail as not to unnecessarily obscure aspects of the present invention. In the light of the foregoing background, it is an object of the present invention to provide a testing device for verifying the performance of a non-invasive physiological information detecting device, e.g., a pulse oximeter.

In one embodiment, a testing device is designed to verify the performance of the non-invasive physiological information detecting device, e.g., a pulse oximeter, which is operable to detect the physiological information of the user via a non-invasively optical manner. The physiological information may include, but not limited to, the blood oxygen saturation, pulse rate, blood pressure, etc. The physiological information detecting device could detect the physiological information at any location of the user, e.g., finger, wrist or other part of the body. In one embodiment, the non-invasive physiological information detecting device detects the physiological information at the finger-tip or finger knuckle of the user by clamping or wearing the device on the fingertip or finger knuckle. It will be understood that the non-invasive physiological information detecting device could be of any structure or configuration as long as it satisfies the functional requirement of detecting physiological information of the user via an optical manner.

During the verification/test, the measurement result, e.g., the measured oxygen saturation (SpO2), measured pulse rate (PR) and/or measured perfusion index (PI), of a qualified non-invasive physiological information detecting device should be within predetermined tolerant ranges. If the test result of the non-invasive physiological information detecting device is out of tolerant ranges, this implies the device may need repair or resetting before going into service.

In one embodiment, the testing device is operated by optically modulating the emitted light from the non-invasive physiological information detecting device and conducting the modulated light to the photo-detector of the non-invasive physiological information detecting device. The modulation settings of the testing device are mainly referred to the one or more target physiological values such as target SpO2, PR and/or PI values, which is/are used to be compared with the measurement values of the non-invasive physiological information detecting device in order to verify its performance as manufacturer design. As can be understood by one still in the art, the optical modulation or light presented hereinafter could also represent for any modulation method on electromagnetic signal or any electromagnetic signal which could be used for non-invasive measurement for healthcare.

FIG. 1 shows an exemplary drawing of a testing device 100 being operable to verify the performance of a non-invasive physiological information detecting device, in accordance with one embodiment of the invention. As shown in FIG. 1, the testing device comprises a main body 101 being configured to be coupled to a physiological information detecting probe 102, e.g., a pulse oximeter probe, to verify the performance of the probe 102. For easy understanding and description, the non-invasive physiological information detecting device will be described as a pulse oximeter hereinafter. As can be understood by one skill in the art, the pulse oximeter hereinafter could represent for any device or equipment for non-invasively detecting the healthcare information of the user.

In one embodiment, the testing device could be attached to the pulse oximeter probe 102 or be positioned nearby the pulse oximeter probe 102. In one embodiment, the main body 101 is designed in a shape that could be at least partially positioned within the measuring space of the probe 102. For example, for a transmissive pulse oximeter, the main body 101 will be positioned, at least partially, in between the light emitter and light detector of the optical sensor. For a reflective pulse oximeter, the main body 101 will be positioned, at least partially, nearby the optical sensor within a predetermined distance range there between. In an exemplary embodiment, the main body 101 is designed in a shape that could be inserted into the probe 102 like a real finger. In the exemplary embodiment of FIG. 1, the main body 101, like a normal finger, is inserted through the pulse oximetry probe 102 while a testing window 103 of the main body 101 is nearby an optical sensor 104 of the pulse oximeter probe 102 for receiving light from the optical sensor 104 and conducting the modulated light to the optical sensor 104 in a transmissive or reflective mode, as being more clearly shown in an enlarged sub-drawing of FIG. 1.

In one embodiment, the pulse oximeter optionally comprises a base unit 105 being coupled to the pulse oximeter probe 102 for supporting the probe 102, reading the detecting data from the probe 102, processing the detecting data and displaying the final result as the target physiological value, e.g., the blood oxygen saturation value and/or pulse rate value. During the verification test, the measurement result of the pulse oximeter probe 102 will be compared, in a manual or automatic way, with the target physiological value corresponding to the current modulation setting of the testing device 100. If the measurement result is far from the target value, which means the measurement result of the pulse oximeter is not accurate, the pulse oximeter fails the verification test and may need to be repaired or reset before going into service.

In one embodiment, the testing device 100 further comprises a stopper 106 and a flexible unit 107, e.g., a spring, being positioned at the front and end of the pulse oximeter to fix the pulse oximeter during the verification process. In the exemplary embodiment, when to couple the pulse oximeter probe 102 to the main body 101, the base unit 105, which holds and supports the probe 102, is put in between the stopper 106 and the flexible unit 107 by backwardly pushing the flexible unit 107. Then the flexible unit 107 will push the base unit 105 until reaching the stopper 106 so as to fix the base unit 105 as well as the probe 102 while guiding the pulse oximeter probe 102 to be properly coupled to the main body 101.

As would be understood to one skill in the art, the testing device 100 shown in FIG. 1 is for illustration purpose, and the structure and configuration of the testing device 100, as well as its main body 101, are not limited to the exemplary embodiment of FIG. 1, but can have various shapes/structures as long as it satisfies the function of verifying the performance of the pulse oximeter.

Figure 2:
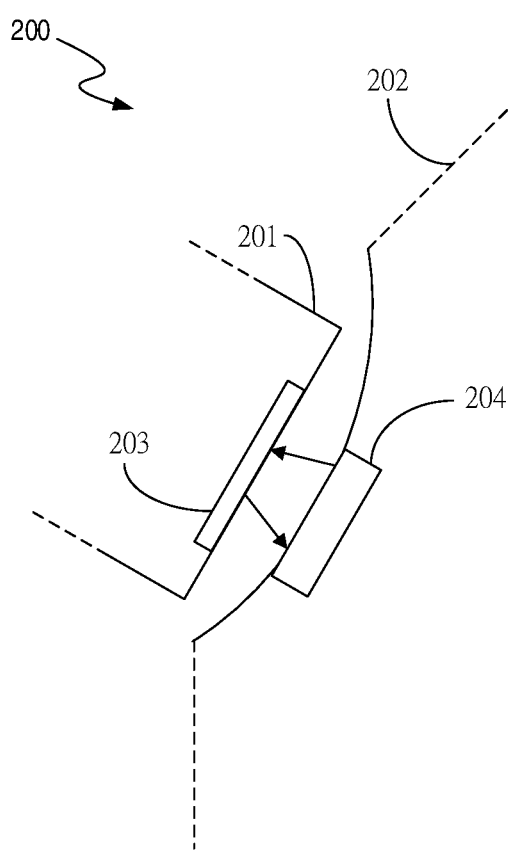
FIG. 2 shows a position relationship 200 between the testing device and the non-invasive physiological information detecting device, in accordance with one embodiment of the invention.

FIG. 2 shows a position relationship 200 between the testing device and the pulse oximeter, in accordance with one embodiment of the invention. Elements with the same or similar reference numerals in FIG. 2 have the same or similar structure/function as thereof in previous figures. As shown in FIG. 2, when a reflective pulse oximeter 202 is coupled to a testing device 201 for verifying its performance, a window 203 of the testing device 201 is aligned with an optical sensor 204 of the pulse oximeter 202 for receiving the light emitted from the optical sensor 204 and enable the modulated light being transmitted to the optical sensor 204 via the window 203. It is understood by one skilled in the art that the dotted line of the testing device 201 and the pulse oximeter 202 means for the unlimited shapes or structures of the testing device 201 and the pulse oximeter 202. The drawing is just used to illustrate the positional relationship between the testing device and the pulse oximeter during the verification process. The real shapes or structures of the testing device and the pulse oximeter are not limited to the drawing of FIG. 2 but can be various shapes/structures as long as the window of the testing device is aligned with, or at least partially aligned with, the optical sensor of the pulse oximeter. Although a reflective pulse oximeter is depicted here for illustration, the testing device could be also used for the transmissive pulse oximeter that an input and an output window of the testing device are respectively aligned with, or at least partially aligned with, the light emitter and light detector of the pulse oximeter.

Figure 3:
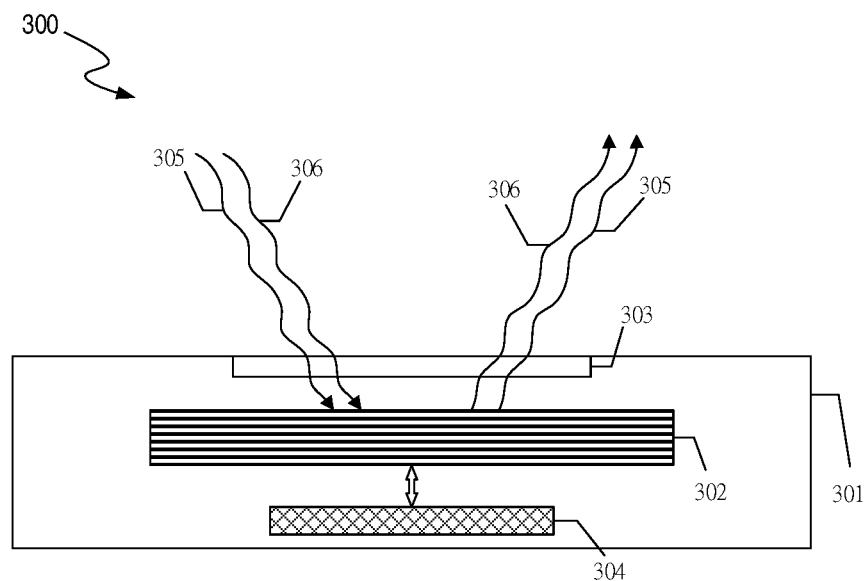
FIG. 3 illustrates a schematic structure of a testing device for verifying the performance of a non-invasive physiological information detecting device, in accordance with one embodiment of the invention.

FIG. 3 illustrates a schematic structure of a testing device for verifying the performance of a pulse oximeter, in accordance with one embodiment of the invention. FIG. 3 will be described in combination with FIG. 1. In FIG. 3, the testing device is used to verify the pulse oximeter in a reflective mode, which means the optical sensor of the pulse oximeter will detect the light signal reflected from the user which carries the physiological information of the user so as to obtain the user's physiological information via the light signal. For simplifying the illustration, the FIG. 3 mainly shows the structure of a main body 300 of the testing device, e.g., the main body 101 in FIG. 1, without the other mechanical designs. In the substrate 301 of the main body 300, the window 303 is configured on the top surface of the substrate 301 for receiving the light emitted from the pulse oximeter and enable the modulated light being transmitted to the pulse oximeter via the window 303. Furthermore, a modulating unit 302 is configured within the substrate 301 under the window 303 for modulating the light received through the window 303 and returning the modulated light back to the pulse oximeter via the window 303. In one embodiment, two kinds of emitted light 305 and 306 from the pulse oximeter will be received at the modulating unit 302. The light 305 and 306 could be two kinds of light with different wavelengths, e.g., a red light with the wavelength in between 600 to 800 mm and an infrared light with the wavelength in between 800 to 1000 mm. The modulating unit 302 will modulate the two kinds of light 305 and 306 and return two kinds of the modulated light 305 and 306 to the pulse oximeter.

Within the substrate 301 of the main body 300, a driving circuit 304 is coupled to the modulating unit 302 for driving the modulating unit 302 to modulate the receiving light. When the pulse oximeter is coupled to the testing device, the light emitted from the pulse oximeter will enter into the main body 300 through the window 303 until reaching the modulation unit 302. The driving circuit 304 will drive the modulating unit 302 to modulate the received light in a predetermined modulation manner to simulate changes of the light signal through the blood vessel during the real physiological information detection in light absorption at a real blood vessel which refers to a target physiological value, e.g., target blood oxygen saturation value and/or target pulse rate. In one embodiment, the modulation manner is predetermined by the target physiological value. Thereafter, the modulated light will be returned back to the pulse oximeter via the winder 303. The pulse oximeter processes the detected light to obtain the measured physiological value. The measured physiological value will be compared with the target physiological value to verify the performance of the pulse oximeter. In one embodiment, the driving circuit 304 can further tune and adjust the parameters of the modulating unit 302 so as to enable the modulating unit 302 to modulate the light in multiple modulation manners that respectively refer to multiple target physiological values. By comparing the measured physiological value of the pulse oximeter derived from the detected light, which is modulated in a modulation manner, with a target physiological value, which corresponds to the subject modulation manner, it is able to verify whether the measurement of the pulse oximeter is accurate.

As can be understood by one skilled in the art, the internal configuration of the main body 300 of the testing device is not limited to the structure shown in FIG. 3 but can be any configuration as long as it satisfies the aforesaid function. For example, the driving circuit 304 could be configured at a lateral side of the substrate 301 while coupled with the modulating unit 302 for driving it. Furthermore, the modulating unit 302 could be configured in any shape under the window 303 to receive and modulate the light emitted from the pulse oximeter.

Figure 4:
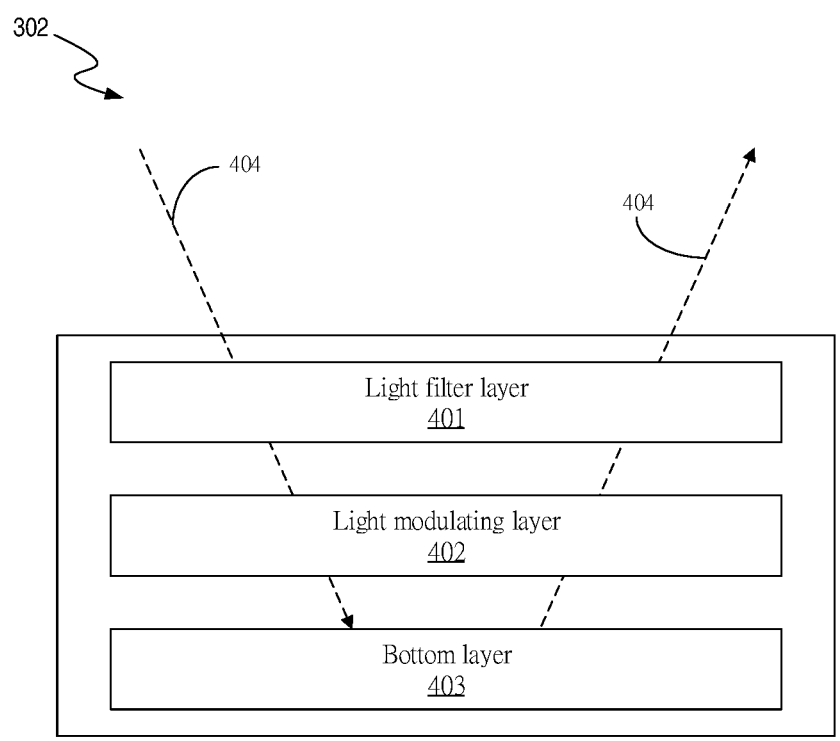
FIG. 4 illustrates a schematic structure of the modulating unit 302, in accordance with one embodiment of the invention.

FIG. 4 illustrates a schematic structure of the modulating unit 302, in accordance with one embodiment of the invention. FIG. 4 will be described in combination with FIGS. 1-3. As shown in FIG. 4, the modulating unit 302 comprises three layers distributed from top to bottom. The top layer is a light filter layer 401 for selectively filtering the emitted light 404 and outputting a target light with a specified wavelength. In one embodiment, the emitted light 404 is a mixed light comprising visible light (e.g., red light) and invisible light (e.g., IR light). The light filter layer 401 will filter the mixed light 404 and output one kind of light within the mixed light for further use according to different embodiments. A light modulating layer 402 is configured under the light filter layer 401 to receive the filtered light 404 from the filter layer 401 and modulate the light 404 in a specified manner to simulate the real change in the light signal through the blood vessel.

Under the light modulating layer 402, a bottom layer 404 is presented to conduct the modulated light 404 to the pulse oximeter via a predefined path or absorb the useless light passing through the light modulating layer 402. In a specified embodiment, the bottom layer 404 will conduct the modulated light 404 to return back to the pulse oximeter in a substantially reversed direction with respect to the light emitting direction.

The layer configuration shown in FIG. 4 is for abstract illustration purposes to show a general functional arrangement of the layers. Different embodiments of the modulating unit 302 could have variant layer configurations. In an exemplary embodiment, two or more packs of the subject layers may be stacked to modulate different light within different ranges of wavelengths, e.g., red light and IR light. In another exemplary embodiment, the filter layer 401 may be positioned under the light modulating layer 402. More detailed embodiments will be illustrated by the following description and drawings.

Generally, the blood oxygen saturation level (SpO2) is measured based on changes in light absorption of two kinds of light in the blood vessel of the user. In one embodiment, the two kinds of light include a red light and an Infrared light. During the measurement, the DC component of the detected light signal is attributable to the bulk absorption of the skin tissue, while the AC component of the detected light signal is attributable to variations in blood volume of the blood vessel caused by the pressure pulse of the cardiac cycle. In one embodiment, the AC component of the detected light signal is attributable to the variation in blood volume of the artery. The SpO2 will be calculated based on the detected light signal by the equations given below:

$$R = (ACrms \text{ of } Red/DC \text{ of } Red)/(ACrms \text{ of } IR/DC \text{ of } IR) \quad \text{(Equation 1)}$$

$$\% \, SpO_2 = 110 - 25 \times R \quad \text{(Equation 2)}$$

wherein ACrms of Red is the AC component of a first light modulated via the blood vessel, ACrms of IR is the AC component of a second light modulated via the blood vessel, DC of Red is the DC component of the first light modulated via the blood vessel, DC of IR is the DC component of the second light modulated via the blood vessel, and SpO2 is the blood oxygen saturation level. In one embodiment, the first light is red light and the second light is infrared light. As can be understood by one skilled in the art, the SpO2 could be calculated based on the value R by using alternative function model, and not limited to the equation as listed above.

Figure 5A:
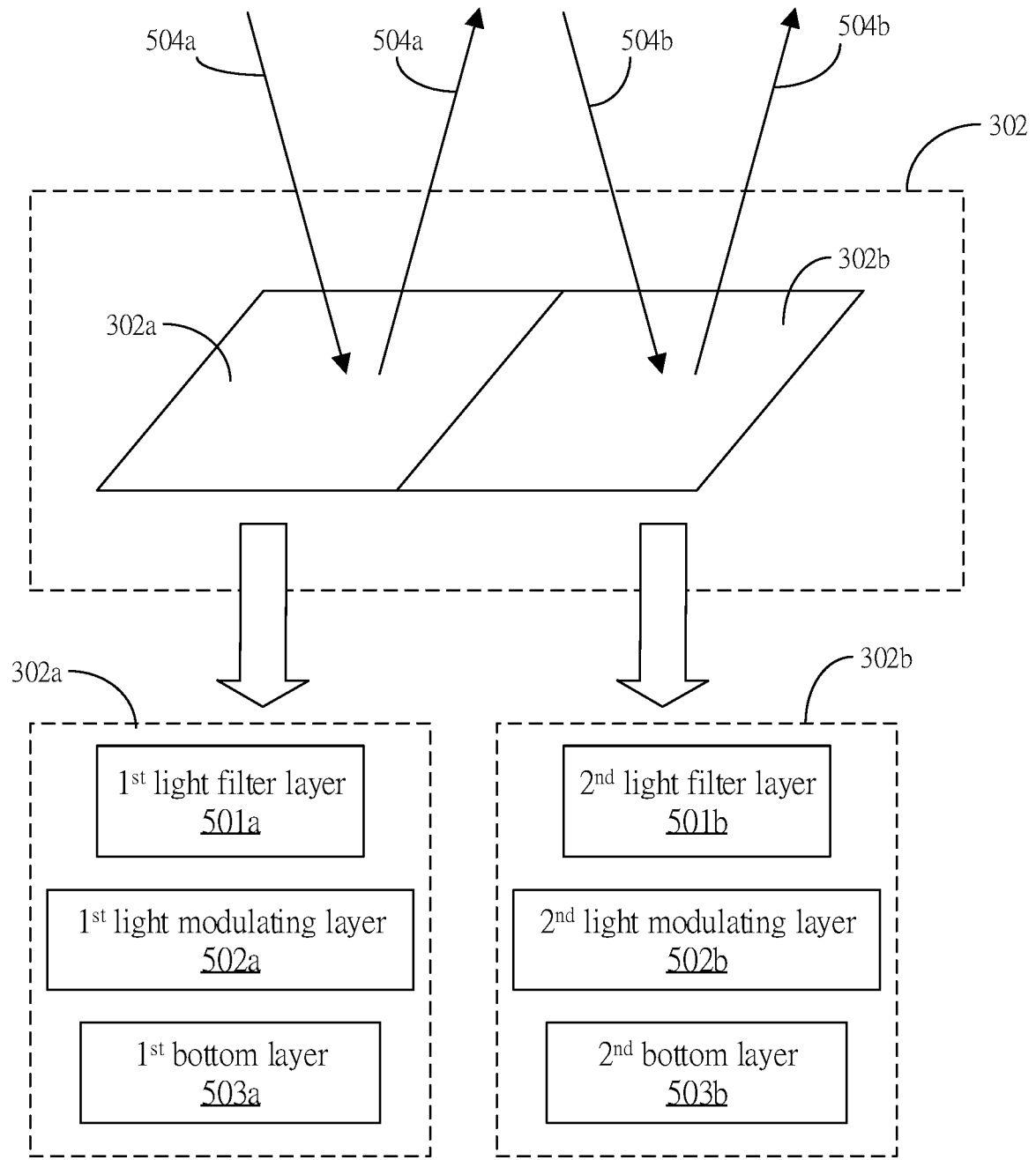
FIG. 5A illustrates a detailed structure of the modulating unit 302, in accordance with one embodiment of the invention.

In one embodiment, the modulating unit 302 modulates the two kinds of emitted light to simulate the changes in light absorption ratio of the two kinds of emitted light, i.e., ACrms of Red/DC of Red, and/or Acrms of IR/DC of IR, via blood vessel for building a target SpO2 value. Furthermore, the modulated light could also be used to build other physiological information, e.g., pulse rate and/or perfusion index. FIG. 5A illustrates a detailed structure of the modulating unit 302, in accordance with one embodiment of the invention. FIG. 5A will be described in combination with FIGS. 1-4. In the subject modulating unit 302, two sub-modulating units 302a and 302b are arranged side by side while in contact with or being separate from each other. In preferred embodiment, the sub-modulating units 302a and 302b are aligned with each other as shown in FIG. 5A. However, as understood by one skilled in the art, the two sub-modulating units 302a and 302b could also be misaligned with each other as long as each will not affect the light modulation of the other one.

In one embodiment, the first sub-modulating unit 302a filters the emitted light to get a first light 504a, and then modulate the first light 504a and conduct the modulated light 504a back to the pulse oximeter. The second sub-modulating unit 302b filters the emitted light to get a second light 504b, and then modulates the second light 504b and conducts the modulated light 504b back to the pulse oximeter. In one embodiment, the first light 504a is red light and the second light 504b is infra-red (IR) light. During the operation, a mixed light comprising a first and second light are emitted from the pulse oximeter to the modulating unit 302. As such, a first light filter layer 501a is disposed on the top of the first sub-modulating unit 302a to filter the received mixed light to output the first light 504a to a following light modulating layer 502a. A second light filter layer 501b is disposed on the top of the second sub-modulating unit 302b to filter the received mixed light to output the second light 504b to a following light modulating layer 502b. In one embodiment, the first light is red light and the second light is IR light. The first light filter layer 501a is a red light bandpass filter and the second light filter layer 501b is an IR light bandpass filter. In another embodiment, the first filter layer 501a or the second filter layer 501b is a first functional filter or a second functional filter, wherein the first functional filter is operable to enable target light to pass through while absorbing the unwanted light, e.g., the absorptive filter. The second functional filter is operable to enable the target light to pass through while reflecting the unwanted light, e.g., the dichroic filter.

In one embodiment, the first light modulating layer 502a is operable to modulate the first incident light 504a to simulate the light absorption condition of the first light 504a at a real blood vessel. The second light modulating layer 502b is operable to modulate the second incident light 504b to simulate the light absorption condition of the second light 504b at the real blood vessel. The light modulation of the first and second incident light 504a and 504b via the light modulating layer 502a and 502b are determined based on a target SpO2 value. That means in order to obtain the target SpO2 value, the first light 504a and the second light 504b are modulated by the respective first and second light modulating layers 502a and 502b in a corresponding manner. With the modulated light 504a and 504b, the SpO2 value calculated based on the above equations should be substantially equal to the target SpO2 value. Thereafter, the modulated light 504a and 504b will be processed by a bottom layer. In one embodiment, a first bottom layer 503a will conduct the first modulated light 504a back to the pulse oximeter in a substantially reversed direction with respect to a light emitting direction of the pulse oximeter. A second bottom layer 503b will conduct the second modulated light 504b back to the pulse oximeter in a substantially reversed direction with respect to the light emitting direction of the pulse oximeter. In alternative embodiment, the first and second bottom layers 503a and 503b will absorb the useless light passing through the light modulating layers 502a and 502b.

Figure 6A:
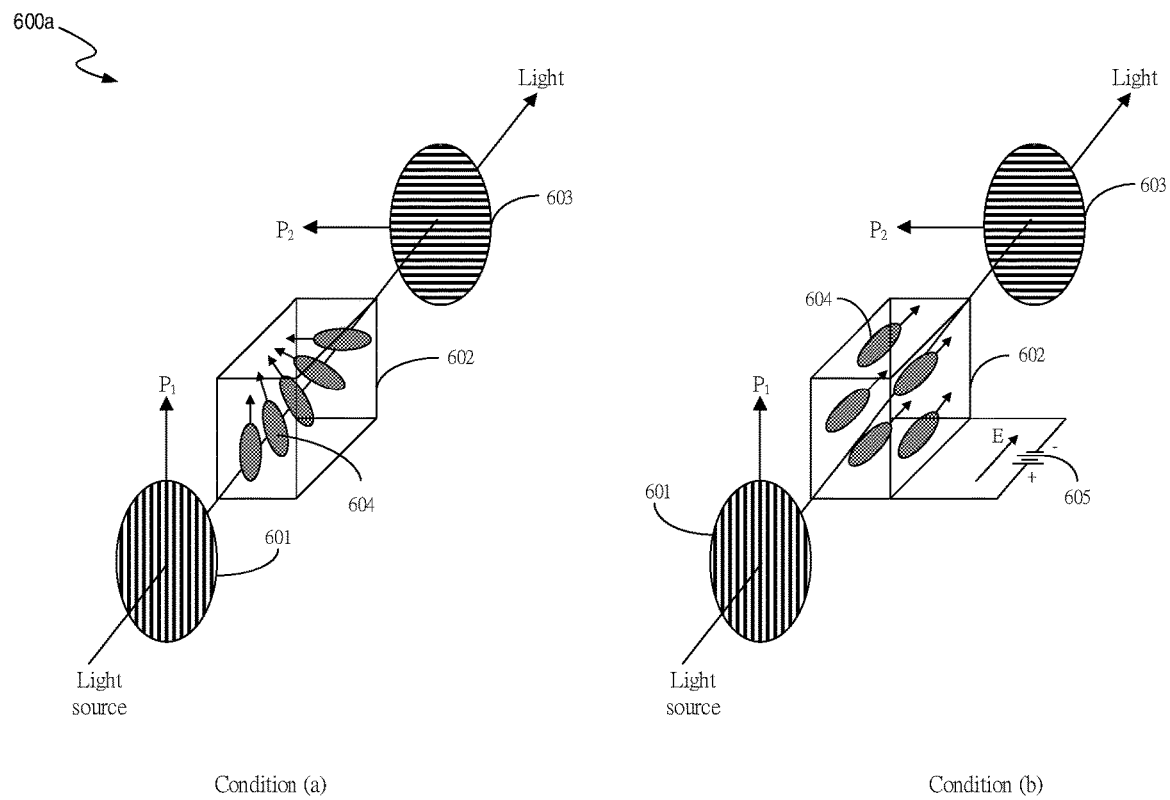
FIG. 6A illustrates a liquid crystal panel 600a being operable for light modulation, in accordance with one embodiment of the invention.

In one embodiment, the light modulating layer, i.e., the light modulating layer 502a or 502b, is a liquid crystal panel 600a as illustrated by FIG. 6A. In one embodiment, the liquid crystal panel 600a comprises a first polarizer layer 601, a liquid crystal layer 602 and a second polarizer layer 603, wherein the liquid crystal layer 602 sits between the two polarizer layers 601 and 603 that are crossed, that is, an orientation Pi of the first polarizer layer 601 is perpendicular to an orientation P2 of the second polarizer layer 603. The alignment of liquid crystal molecules 604 in the liquid crystal layer 602 is chosen so that its relaxed phase is a twisted one (condition (a) in FIG. 6A). This twisted phase reorients the light that passes through the first polarizer layer 601, allowing its transmission through the second polarizer layer 603. When an electric field 605 is applied to the liquid crystal layer 602 (condition (b) as shown in FIG. 6A), axes of the liquid crystal molecules 602 tend to be aligned in parallel with a direction of the electric field 605 thus gradually untwisting in the center of the liquid crystal layer 602. In one embodiment, the electric field 605 is provided by the driving circuit 304. In this state, the liquid crystal molecules 604 do not reorient light when the light pass through the liquid crystal layer 602, so the light, that is polarized by the first polarizer layer 601, passing through the liquid crystal layer 602 and reaching the second polarizer layer 603, is in an orientation perpendicular to the orientation of the second polarizer layer 603. Hence the light will be essentially absorbed by the second polarizer layer 603 and cannot pass through it. The absorption ratio of the light at the second polarizer layer 603 will increase with increasing voltage of the electric field 605.

Under such condition, by controlling the electric field 605, the absorption frequency and ratio of the incident light could be accordingly varied in a predetermined manner to form an alternating current (AC) optical signal in a predetermined waveform, e.g., like the waveform of a photoplethysmography signal, so as to simulate the real condition of the light absorption ratio (AC part/DC part) of the subject light via the blood vessel. In other words, the liquid crystal panel 600a will be controlled to absorb the light passing through it in a predetermined manner for light modulation.

It will be understood by one skill in the art that the liquid crystal panel 600a can have various shapes and configurations without departing from the scope of example embodiment.

With such configuration of the light modulating layer shown in FIG. 6A, the corresponding bottom layer will be a light reflective layer to reflect the light, which output from the second polarizer layer 603, back to the pulse oximeter. In one embodiment, the light reflective layer is a mirror to reflect all the light back to the pulse oximeter. In another embodiment, the light reflective layer is the second functional filter to reflect back the target light with the specified wavelength, while letting the unwanted light with other wavelength to pass through the bottom layer. In an exemplary embodiment, the light reflective layer could be a dichroic filter. As can be understood by one skilled in the art, the light reflective layer could be any material/configuration as long as it satisfies the function of light reflection.

In an alternative embodiment, the light modulating layer, i.e., the light modulating layer 502a or 502b, is a liquid crystal panel 600b as illustrated by FIG. 6B. In one embodiment, the liquid crystal panel 600b is a polymer dispersed liquid crystal panel that comprises simple micro droplets of liquid crystals 607 encapsulated in a polymer matrix 608. The liquid crystals 607 respond to an electrical charge. In a static state (a), the liquid crystal molecules 607 remain in a randomized configuration that refracts the incident light that enters the matrix 608, wherein some incident light may pass through the polymer matrix 608 while most incident light is scattered by the liquid crystal molecules 607 and returns back to the pulse oximeter in what is now essentially a scattering state. When electricity is applied, the molecules 607 line up with the direction of the electric field 609, allowing light to pass through the polymer matrix 608 what is now essentially a transmissive state. In one embodiment, the electric field 609 is provided by the driving circuit 304. When electrical charge is deactivated, liquid crystal droplets 607 again become randomly oriented, the incident light is again heavily scattered and does not pass through in a straightforward manner, resulting in the scattering state. By increasing the voltage of the electric field 609 applied to the liquid crystal panel 600b, the scattering rate of the light that returns back to the pulse oximeter will be decreased.

Similarly, by controlling the electric field 609, the scattering ratio of the incident light could be accordingly varied such that the light scattered by the liquid crystal panel 600b and back to the pulse oximeter will be modulated to form an AC optical signal in a predetermined waveform, e.g., like the waveform of a photoplethysmography signal, so as to simulate the real condition of the light absorption ratio (AC part/DC part) of the subject light via the blood vessel. In other words, the liquid crystal panel 600b will be controlled to scatter the incident light in a predetermined manner for light modulation.

As can be understood by one skilled in the art, the liquid crystal layer 600b can have various shapes and sizes without departing from the scope of example embodiment.

With such configurations of the light modulating layer shown in FIG. 6B, the corresponding bottom layer will be a light absorptive layer to absorb the unwanted light passing through the polymer matrix 608 in order to avoid any impact caused by the useless light.

In a further alternative embodiment, the light modulating layer, i.e., the light modulating layer 502a or 502b, is a digital mirror device 600c as illustrated by FIG. 6C. In one embodiment, the digital mirror device 600c comprises a reflector 610, e.g., a mirror, for reflecting the incident light in a certain direction. The mirror 610 could be rotated to reflect the incident light in different directions as shown in dotted line arrows of FIG. 6C. A controlling unit 611 is operable for controlling the rotating angle of the mirror 610 via a rotating unit 612. By adjusting the rotating angle of the mirror 610, the reflecting direction of the reflected light could be changed. Since the intensity of the light signal reaching the optical sensor 104 of the pulse oximeter 102 will vary with different reflecting directions of the reflected light, by controlling the rotating angle of the mirror 610, the direction of the reflected light could be accordingly varied such that the intensity of the light signal detected at the optical sensor 104 will be changed in a predetermined manner to form an alternating current (AC) optical signal in a predetermined waveform, e.g., like the waveform of a photoplethysmography signal, so as to simulate the real condition of the light absorption ratio (AC part/DC part) of the subject light via the blood vessel. In other words, the digital mirror device 600c will be controlled to reflect the incident light in a predetermined manner for light modulation.

As can be understood by one skilled in the art, the digital mirror device 600*c* can have various shapes and sizes without departing from the scope of the example embodiment.

With such configurations of the light modulating layer shown in FIG. 6C, the corresponding bottom layer could be omitted or seen as combined with the light modulating layer.

In one embodiment, the light modulating layer 502*a* and 502*b* in FIG. 5A could be any one of the liquid crystal panel 600*a* and 600*b* and the digital mirror device 600*c* as shown in FIG. 6A, 6B and 6C with the following bottom layer being set to reflect or absorb light or being combined with the light modulating layer. For example, if the light modulating layer 502*a* or 502*b* is the liquid crystal panel 600*a* in FIG. 6A, then a light reflective layer 503*a* or 503*b* will be disposed under the light modulating layer 502*a* or 502*b* to reflect the light, which passes through the light modulating layer 502*a* or 502*b*, back to the pulse oximeter. If the light modulating layer 502*a* or 502*b* is the liquid crystal panel 600*b* in FIG. 6B, then a light absorptive layer 503*a* or 503*b* will be disposed under the light modulating layer 502*a* or 502*b* to absorb the unwanted light, which passes through the light modulating layer 502*a* or 502*b*, to avoid any impact caused by the unwanted light. If the light modulating layer 502*a* or 502*b* is the digital mirror device 600*c* in FIG. 6C, then the bottom layer could be omitted accordingly. Furthermore, if the light modulating layer 502*a* or 502*b* is the liquid crystal panel 600*a* in FIG. 6A, the corresponding light filter layer 501*a* or 501*b* may be omitted if the polarizer layers 601 and/or 603 of the liquid crystal panel 600*a* are set to function as light filters.

Figure 5B:
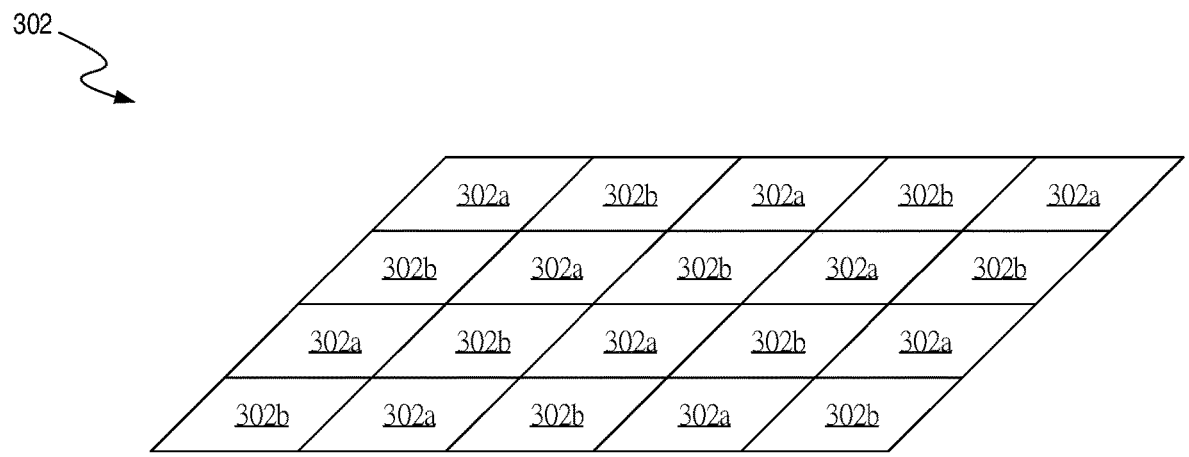
FIG. 5B illustrates an exemplary schematic structure of an array of multiple sub-modulating units within the modulating unit 302, in accordance with one embodiment of the invention.

In another embodiment, the modulating unit 302 comprises multiple sub-modulating units, e.g., an array of the sub-modulating units, being disposed under the window 303 to modulate the incident light and conduct the modulated light back to the pulse oximeter in a more homogeneous way. More specifically, the modulating unit 302 comprises multiple sub-modulating units being arranged in a pattern that the first sub-modulating unit 302*a* and the second sub-modulating unit 302*b* are disposed in a substantially alternative way. In one embodiment, as illustrated in FIG. 5B, the first sub-modulating units 302*a* and the second sub-modulating units 302*b* are alternatively arranged to respectively modulate the first and second light and conduct the modulated first and second light back to the pulse oximeter. Under such condition, the light returned to the pulse oximeter could be homogeneously mixed with the first and second light to eliminate the impact caused by any deviation in direction of the incident light emitted from the pulse oximeter probe 102. In one embodiment, the sub-modulating units are separated from each other, which means each sub-modulating unit has its own light filter layer 501*a*/501*b*, light modulating layer 502*a*/502*b* and bottom layer 503*a*/503*b*. Under such configuration, each sub-modulating unit could be individually tuned by providing respective electrical field to simulate multiple physiological values, e.g., SpO2 value, pulse rate value and/or perfusion index value. In one exemplary embodiment, the light modulating layers 502*a*/502*b* of the sub-modulating units could be the liquid crystal panel 600*a*, the liquid crystal panel 600*b* or the digital mirror device 600*c*, and the bottom layer 503*a*/503*b* will correspondingly be the light reflective layer or the light absorptive layer or omitted. In another embodiment, the sub-modulating units only have the separated and individual light filter layers 501*a*/501*b*, but share a common light modulating layer and bottom layer. Under such condition, the driving circuit as well as the whole configuration could be simplified but the light modulating layer could not be separately tuned for each sub-modulating unit and only one or limited physiological values could be achieved.

As can be understood by one skill in the art, the pattern and configuration of the sub-modulating unit array are not limited to the illustrated embodiment but could have alternative embodiments within the scope and spirit of the presented invention. For example, the sub-modulating unit array could have only one row or one column or a matrix. The first and second sub-modulating units could be alternatively arranged in an arbitrary way while satisfying the function of uniformly modulating and mixing the light. For example, every two first sub-modulating units (1) and every three second sub-modulating units (2) are alternatively arranged like 1122211222, or one first sub-modulating unit, two second sub-modulating units, three first sub-modulating units, and two second sub-modulating units are alternatively arranged like 12211122. Furthermore, the light filter layers and the light modulating layers of the sub-modulating units 302*a*/302*b* are separated and individual units while share a common bottom layer, in one embodiment. In an alternative embodiment, the light filter layers and the bottom layers of the sub-modulating units 302*a*/302*b* are separated and individual units while sharing a common light modulating layer.

Figure 7A:
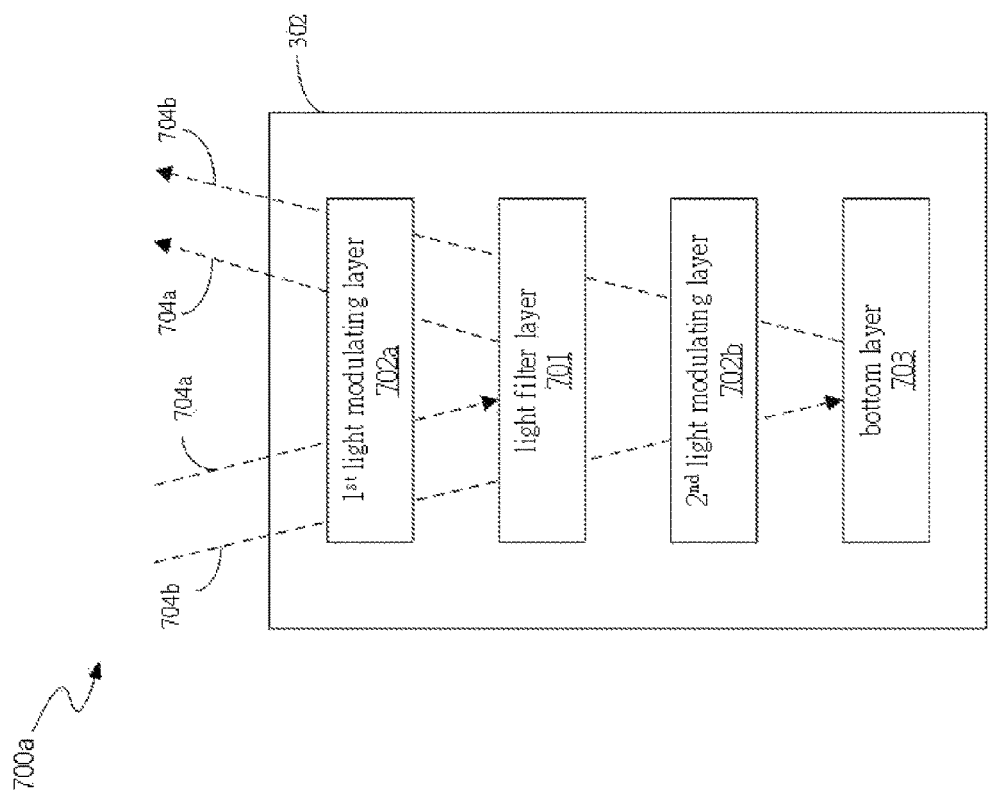
FIG. 7A illustrates a structure 700a of the modulating unit 302, in accordance with one embodiment of the invention.

FIG. 7A illustrates a structure 700*a* of the modulating unit 302, in accordance with one embodiment of the invention. FIG. 7A will be described in combination with FIGS. 1-6. As comparing with FIG. 5A, in the modulating unit 302 of FIG. 7A, the incident light emitted from the non-invasive physiological information detecting device, including a first light 704*a* and a second light 704*b*, will be respectively modulated by two light modulating layers being vertically stacked in a direction along the incident light axis. In one embodiment, the detecting light including the first light 704*a* and the second light 704*b* is entered into a first light modulating layer 702*a*. The first light modulating layer 702*a* will modulate the incident light in a preset manner and output the modulated light to a light filter layer 701. In one embodiment, the first light modulating layer 702*a* is used to modulate the first light 704*a*. In one embodiment, if the first light modulating layer 702*a* is the liquid crystal panel 600*a*, the light filter layer 701 will be the second functional filter which allows the second light 704*b* to pass through it while reflecting the first modulated light 704*a* passing through the liquid panel 600*a* back to the pulse oximeter. In an exemplary embodiment, the light filter layer 701 is a dichroic filter. If the first light modulating layer 702*a* is the liquid crystal panel 600*b*, the light filter layer 701 will be the first functional filter which allows the second light 704*b* to pass through it while absorbing the unwanted first light that passes through the liquid crystal panel 600*b*. In an exemplary embodiment, the light filter layer 701 is an absorptive filter. As described before, the first modulated light 704*a* will be scattered back to the pulse oximeter from the first light modulating layer 702*a*. A second light modulating layer 702*b* will receive the second light 704*b* from the light filter layer 701 and further modulate the second light 704*b* in a preset manner. Thereafter, a bottom layer 703 will reflect the second modulated light 704*b* to the pulse oximeter if the second light modulating layer 702*b* is the liquid crystal panel 600*a* or absorb the useless light passing through the second light modulating layer 702*b* if the second light modulating layer 702*b* is the liquid crystal panel 600*b*. Furthermore, if the second light modulating layer 702*b* is the digital mirror device 600*c*, the bottom layer 703 could be omitted accordingly.

In one embodiment, the light filter layer 701 could be omitted if the first light modulating layer 702a or the second light modulating layer 702b is a first kind of liquid crystal panel 600a of which the first polarizer layer 601 and the second polarizer layer 603 may co-work to selectively modulate one light within a certain range of wavelength, e.g., a visible light, in a preset manner while letting the light beyond the certain range of wavelength, e.g., an infra-red light, to pass through without performing any modulation on it. Furthermore, if the first light modulating layer 702a or the second light modulating layer 702b is a first liquid crystal panel 600a, the other light modulating layer, i.e., the second light modulating layer 702b or the first light modulating layer 702a, will be a second liquid crystal panel 600a or a liquid crystal panel 600b which could modulate multiple kinds of light within multiple ranges of wavelengths, e.g., to modulate both red and IR light, in a preset manner.

Figure 7B:
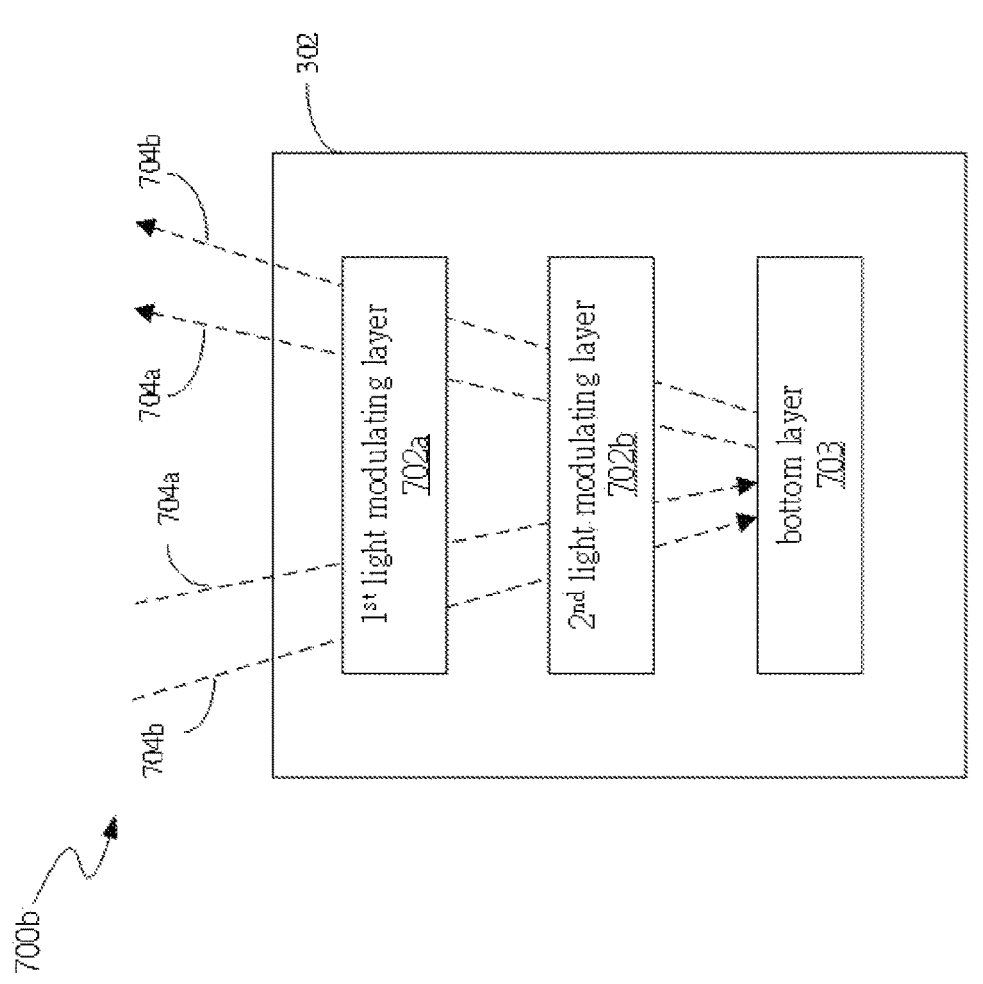
FIG. 7B illustrates another structure 700b of the modulating unit 302, in accordance with one embodiment of the invention.

In an exemplary embodiment 700b, as illustrated by FIG. 7B, the first light modulating layer 702a is the band-limited liquid crystal panel 600a to modulate the first light in a preset manner, and the second light modulating layer 702b is the liquid crystal panel 600b to modulate the first and second light in a preset manner. By properly adjusting the electric fields being applied to the first light modulating layer 702a and the second light modulating layer 702b, the first light modulating layer 702a and the second light modulating layer 702b will respectively modulate the first and second light in multiple manners to simulate different real conditions of light absorption ratio via the blood vessel. In one embodiment, different conditions of light absorption ratio correspond to different physiological values, e.g., SpO2 value, pulse rate value and/or perfusion index value. In one embodiment, the first light 704a is a red light and the second light 704b is an IR light. In one embodiment, the light filter layer 701 could be omitted. The bottom layer 703 will be a light absorptive layer to absorb the unwanted light that passes through the second light modulating layer 702b.

Figure 7C:
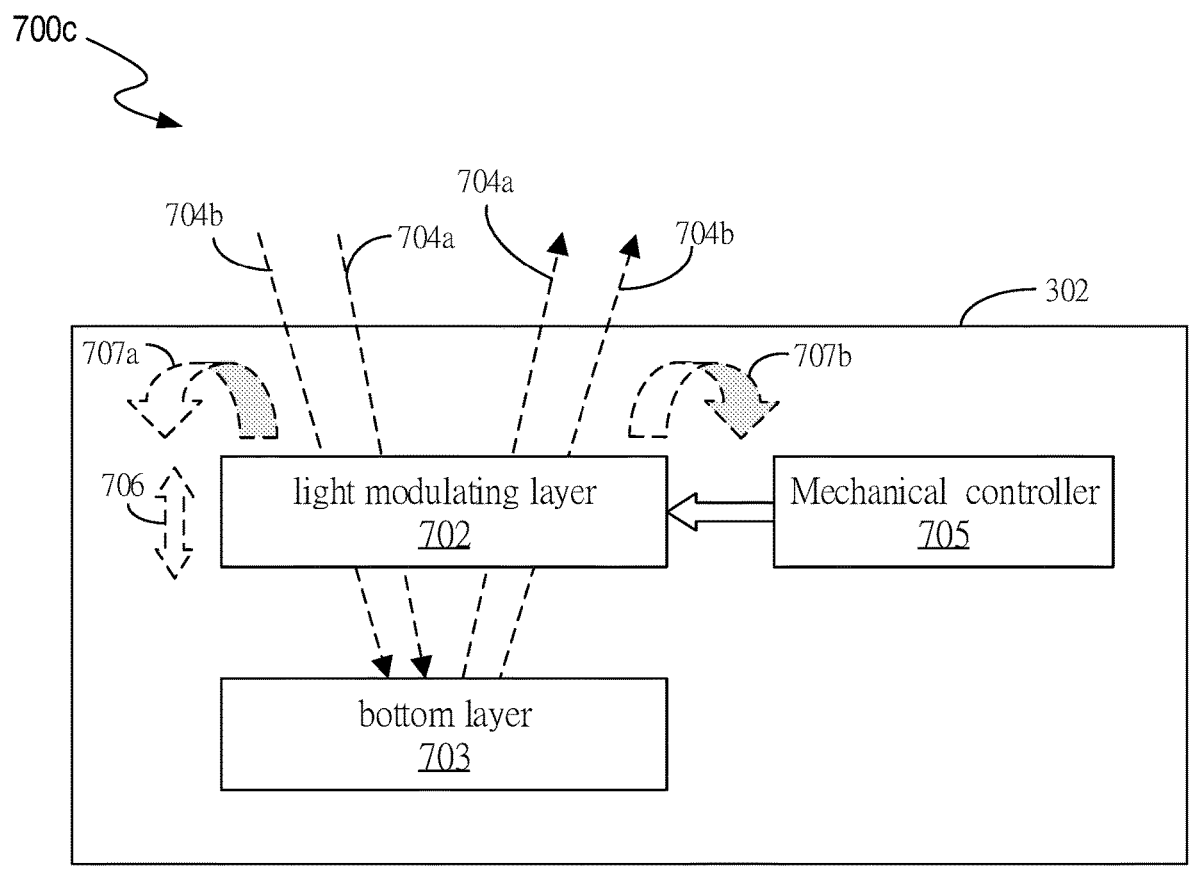
FIG. 7C illustrates another structure 700c of the modulating unit 302, in accordance with one embodiment of the invention.

In another exemplary embodiment 700c, as illustrated by FIG. 7C, the modulating unit 302 comprises a light modulating layer 702 which is a liquid crystal panel 600b having a polymer matrix 608 with liquid crystal molecules 607 inside. The light modulating layer 702 is movable along a direction as indicated by an arrow 706 in dotted line or rotatable in a direction as indicated by two rotation arrows 707a and 707b in dotted line. The modulating unit 302 further comprises a mechanical controller 704 which controls the movement and/or rotation of the light modulating layer 702 in a predetermined manner. For the liquid crystal molecules 607 whose size are within a proper range, the scattering ratio of incident light will vary with the movement and/or rotation of the light modulating layer 702, and the variation of the scattering ratio of different light with different wavelengths caused by the movement and/or rotation of the light modulating layer 702 are different from each other. For example, for two incident light 704a and 704b, e.g., red light and IR light, emitted from the optical sensor to the light modulating layer 702, when the mechanical controller 705 controls the light modulating layer 702 to move in the direction 706 or rotate in the direction 707a or 707b, the change of the scattering ratio (i.e., AC part/DC part) of the first light, e.g., red light, is different from the change of the scattering ratio of the second light, e.g., IR light. Under such condition, by controlling the movement and/or rotation of the light modulating layer 702, multiple SpO2 values could be simulated accordingly for verification. Furthermore, the bottom layer 703 will absorb the unwanted light passing through the light modulating layer 702.

As can be understood by one skill in the art, the configuration of the modulating unit 302 is not limited to the above embodiments, but could have various embodiments within the scope and spirit of the subject invention. For example, the first light modulating layer 702a will modulate both of the first and second light while the second light modulating layer 702b will modulate one of the first and second light, in one embodiment. In another embodiment, the first light modulating layer 702a will modulate the first light while let the second light to pass through. Thereafter the second light modulating layer 702b will modulate the second light. Furthermore, the light path (arrow in dotted line) shown in the figures are for illustration purpose for easily understanding, and not represent the real light path during the use. Moreover, the position of the mechanical controller 705 is not limited to the illustration of FIG. 7C and can be arranged in many formats or positions, e.g., to be embedded in the light modulating layer 702, in one embodiment. In another exemplary embodiment, the mechanical controller could be configured outside the main body 101 to control the movement and/or rotation of the main body 101 such that the light modulating layer 702 within the main body 101 will be moved and/or rotated with respect to the pulse oximeter 102 accordingly, so as to simulate multiple SpO2 values.

In one embodiment, during multiple tests, the control signal for controlling the modulating unit 302 could be adjusted based on different target SpO2 values. In one embodiment, the driving circuit 304 could be controlled based on multiple target SpO2 values, to adjust the electrical field provided to the modulating unit 302 in multiple predetermined modulation configurations corresponding to the multiple target SpO2 values. In another embodiment, the electrical field provided by the driving circuit 304 to the modulating unit 302 is fixed and corresponding to one target SpO2 value.

Furthermore, although FIGS. 5-7 are illustrative for the verification/test on the SpO2 measurement accuracy of the pulse oximeter, the testing device can also be used to verify/test the measurement accuracy of other devices that detect other physiological information of the user by the non-invasive manner in a similar way. In one exemplary embodiment, for verifying the measurement accuracy of a device for detecting the pulse rate and/or perfusion index, the testing device will modulate one kind of signal, e.g., a red light, emitted from the subject device to simulate the real changes of the signal absorption ratio, e.g., the light absorption ratio, via the blood vessel caused by the variant blood volume which responds to the pulse rate and/or perfusion index, and return the modulated signal back to the device. Afterwards, the device will measure the pulse rate and/or perfusion index by detecting the returned modulated signal. By comparing the measured value with the corresponding target value, the measurement accuracy of the pulse oximeter could be verified accordingly.

Figure 8:
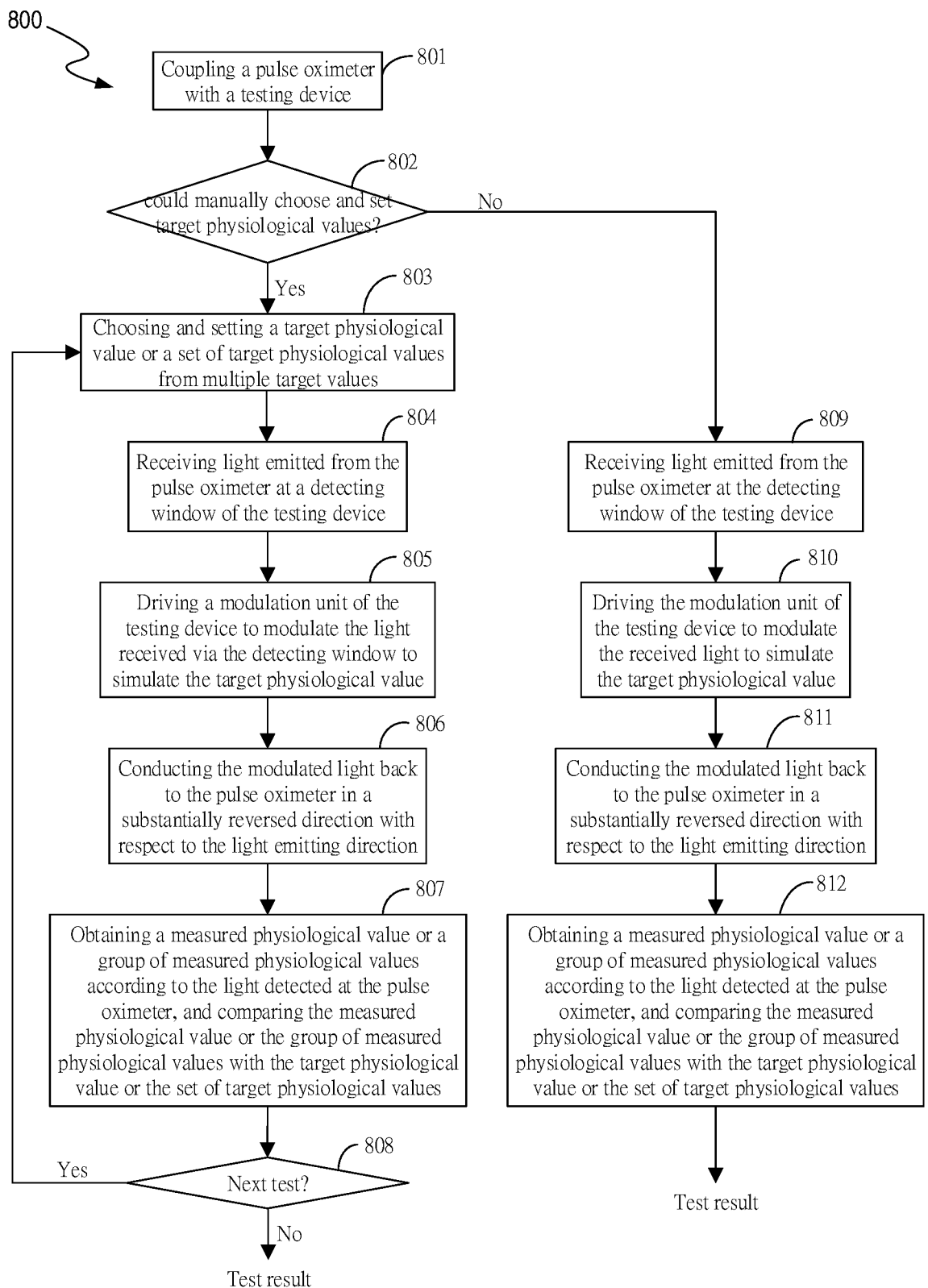
FIG. 8 illustrates a testing flowchart 800 for verifying the performance of a non-invasive physiological information detecting device, in accordance with one embodiment of the present invention.

FIG. 8 illustrates a testing flowchart 800 for verifying the performance of a non-invasive physiological information detecting device, in accordance with one embodiment of the present invention. In the illustrated embodiment shown in FIG. 8, the non-invasive physiological information detecting device is a pulse oximeter. FIG. 8 is described in combination with FIG. 3. In block 801, a pulse oximeter is coupled with a testing device, that means, to make the sensor of the pulse oximeter be aligned with testing window of the testing device. In block 802, if target physiological value could be manually chosen and set in the testing device, the method will go to block 803. In block 803, a target physiological value, e.g., a target SpO2/PR/PI value, or a set of target physiological values, e.g., a set of target SpO2, PR and PI values, are selected from a group of predefined target physiological values and set in the testing device for the current round of verification. In block 804, light emitted from the pulse oximeter is received at a detecting window of the testing device. In block 805, a modulating unit of the testing device is driven to modulate the light received via the detecting window to simulate the target physiological value or the set of the target physiological values. In one embodiment, the absorption frequency and ratio of the received light will be modulated in a preset manner to simulate a real condition of the light absorption ratio via the blood vessel which corresponds to the target physiological value or the set of the target physiological values.

In block 806, the modulated light is conducted back to the pulse oximeter in a substantially reversed direction with respect to the light emitting direction. In block 807, one or more measured physiological values will be obtained according to the returned light detected by the pulse oximeter and then compared with the target physiological value or the set of the target physiological values to verify the measurement performance of the pulse oximeter. In one embodiment, if a difference between the measured physiological value and the target physiological value (or the measured physiological values and the corresponding target physiological values) is less than a predetermined threshold, the measurement accuracy of the pulse oximeter is acceptable. If the subject difference is greater than the predetermined threshold, the pulse oximeter may need to be returned back to the factory for repairing or reset.

In block 808, if a next round of verification is needed, the flowchart will turn to block 803 to select and set a next target physiological value for the next round of verification. If the next round of verification is not needed, the testing flowchart will be ended and the test result will be then be outputted.

In block 802, if a target physiological value or a set of target physiological values are fixed in the testing device, the flowchart will go to block 809. In block 809, similar to block 804, light emitted from the pulse oximeter will be received at the detecting window of the testing device. In block 810, the modulating unit of the testing device will be driven to modulate the received light to simulate the target physiological value or the set of the target physiological values. In block 811, the modulated light will be conducted back to the pulse oximeter in a substantially reversed direction with respect to the light emitting direction. In block 812, one or more measured physiological values will be obtained based on the returned light detected by the pulse oximeter and compared with the target physiological value or the set of the target physiological values to verify the measurement performance of the pulse oximeter. After then, the test result will be outputted.

FIG. 9A illustrates a light modulating method 900a used for verifying the measurement performance of a non-invasive physiological information detecting device, in accordance with one embodiment of the presented invention. FIG. 9A is described in combination with the previous figures. In an illustrated embodiment, the non-invasive information detecting device is a pulse oximeter. As certainly can be recognized by those skilled in the art, the pulse oximeter presented below is just used for illustration. The light modulating method 900a could be properly adjusted, without departing from the spirit and scope of the principles of the present invention, to test other devices that detects the user's physiological information in non-invasive manner. In block 901a, the pulse oximeter emits a mixed detecting light. After then, in block 902a, the mixed light will be filtered by a light filter layer to output one kind of light within a target range of wavelengths for further use. In block 903a, a light modulating layer is driven to modulate the light output from the light filter layer by partially absorbing the light with varying absorption ratios having predetermined changes when the light passes through it. In one embodiment, the light modulating layer is a liquid crystal panel 600a. In one embodiment, a variable electric field is provided to the light modulating layer in order to adjust the absorption ratio of the light therein in a preset manner. In block 904a, the modulated light passing through the light modulating layer will be returned back to the pulse oximeter in a substantially reversed direction with respect to the light emitting direction of the pulse oximeter by a bottom reflective layer.

FIG. 9B illustrates another light modulating method 900b used for verifying the measurement performance of a non-invasive physiological information detecting device, in accordance with another embodiment of the presented invention. In block 901b, the pulse oximeter emits a mixed detecting light. After then, in block 902a, the mixed light will be filtered by a light filter layer to output one kind of light within a target range of wavelengths for further use. In block 903b, a light modulating layer is driven to modulate the light output from the light filter layer. When the filtered light arrives at the light modulating layer, it partially scatters the light back to the pulse oximeter with varying scattering ratios having predetermined changes in a substantially reversed direction with respect to the light emitting direction of the pulse oximeter. In one embodiment, the light modulating layer is a liquid crystal panel 600b. During the light modulation process, a variable electric field is provided to the light modulating layer in order to adjust its scattering ratio of the light in a preset manner. In block 904b, the unwanted light passing through the light modulating layer will be absorbed by a bottom absorptive layer.

FIG. 9C illustrates still another light modulating method 900c used for verifying the measurement performance of a non-invasive physiological information detecting device, in accordance with another embodiment of the presented invention. In an illustrative embodiment, the non-invasive physiological information detecting device is a pulse oximeter. In block 901c, the pulse oximeter emits a mixed detecting light. After then, in block 902c, the mixed light will be filtered by a light filter layer to output one kind of light within a target range of wavelength for further use. In block 903c, a light modulating layer is driven to modulate the light output from the light filter layer by reflecting the light in different directions such that the amount of light arrived at the pulse oximeter, i.e., the intensity of the light signal that could be detected by the pulse oximeter, is varied according to a predetermined manner. In one embodiment, the light modulating layer is a digital mirror device 600c. In one embodiment, the rotating angle of the digital mirror device 600c is adjusted so as to adjust the reflecting direction of the light in a preset manner.

FIG. 9D illustrates still another light modulating method 900d used for verifying the measurement performance of a non-invasive physiological information detecting device, in accordance with another embodiment of the presented invention. In an illustrative embodiment, the non-invasive physiological information detecting device is a pulse oximeter. In block 901d, the pulse oximeter emits a mixed detecting light. In block 902d, the light modulating layer is driven to modulate the mixed light by partially scattering the mixed light back to the pulse oximeter with varying scattering ratios in a substantially reversed direction with respect to the light emitting direction of the pulse oximeter. In block 903d, a distance between the light modulating layer and the pulse oximeter and/or an angle between the light modulating layer and the pulse oximeter is adjusted to differently change the scattering ratio of different kinds of light within the mixed light. In block 904d, the unwanted light passing through the light modulating layer is absorbed by a bottom absorptive layer. As can be understood by one skilled in the art, the above light modulating method is for illustration purposes and the light modulating method could have alternative embodiments without departing from the scope of the example embodiments. For example, the step 902a and 903a or 902b and 903b could be combined with one step such that the filter function and the modulation function could be performed at one time. Furthermore, the method 900a or 900b is not limited for single use but can be combined to process multiple light for simulating the light absorption condition in the blood vessel.

Furthermore, as can be understood by one skilled in the art, the testing device disclosed in the subject invention could be also used for other purposes. For example, the testing device could act as an emulator to emulate a real light modulation condition via the real blood vessel of a living subject that could be used for various verifications. The testing device could be also used as a calibrator being operable to calibrate the measurement result of the pulse oximeter if the measurement deviation of the pulse oximeter is within a reasonable range that can be compensated.

Although the above embodiments mainly refer to the pulse oximeter in a reflective mode, the subject testing device could be also used to verify the performance of the pulse oximeter in a transmissive mode with proper changes on the structure. In one embodiment, an input window and an output window are arranged on different positions of the testing device to receive the emitted light from a light emitter of a pulse oximeter via the input window and transmit the modulated light to a light detector of the pulse oximeter via the output window. Furthermore, the light modulating unit is operable to modulate the light received via the input window and output the modulated light to the output window.

Figure 10A:
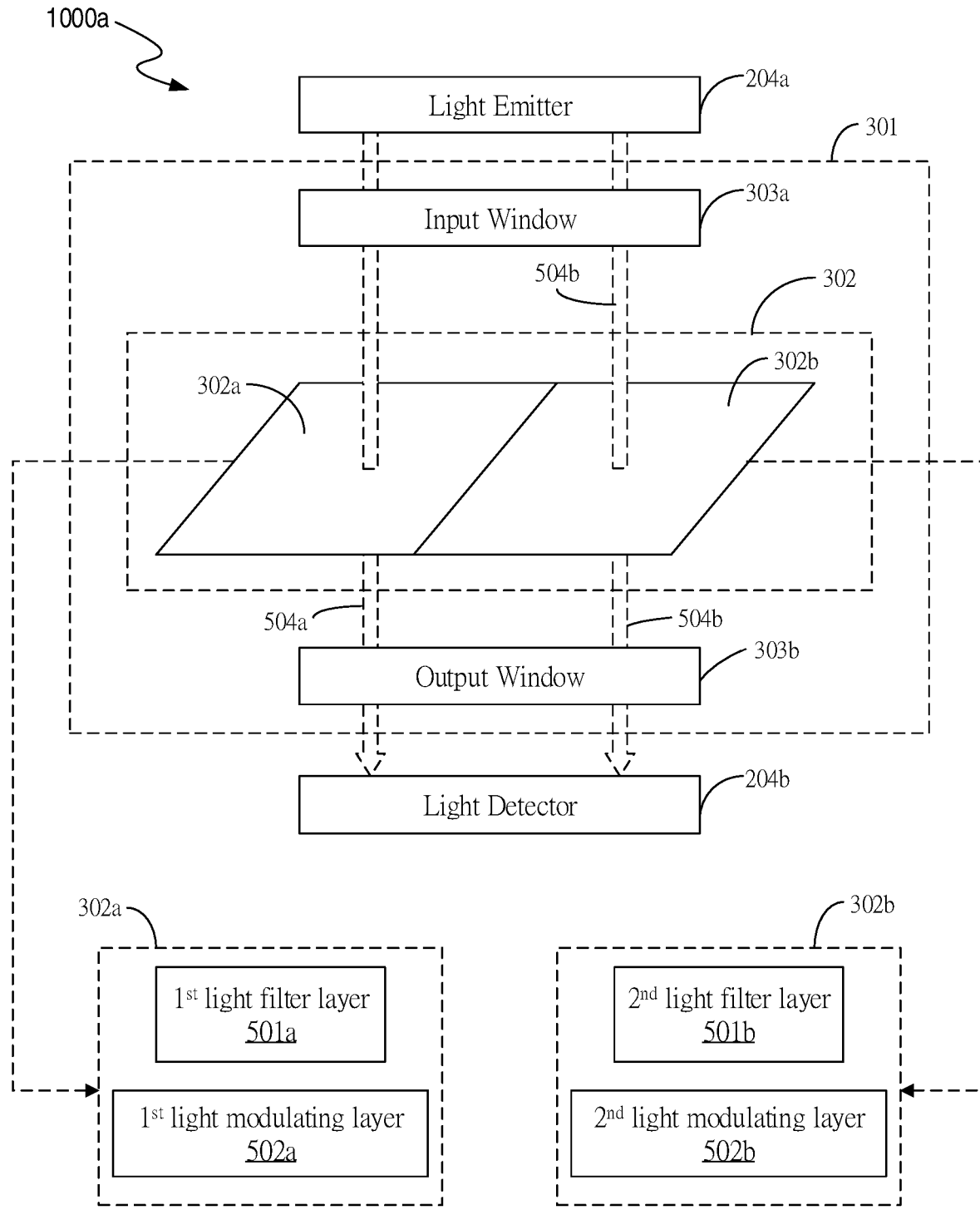
FIG. 10A illustrates a structure of a testing device used for verifying the performance of the non-invasive physiological information detecting device in a transmissive mode, in accordance with one embodiment of the present invention.

FIG. 10A illustrates a structure 1000a of a testing device used for verifying the performance of a non-invasive physiological information detecting device in a transmissive mode, in accordance with one embodiment of the present invention. Elements in FIG. 10A with the same or similar reference numerals have the same or similar structure/function as thereof in previous figures. FIG. 10A will be described in combination with FIG. 5A. As shown in FIG. 10A, the light modulating unit 302 has a similar structure as those illustrated in FIGS. 5A and 5B wherein each of the sub-modulating units 302a and 302b comprises a light filter layer 501a/501b for filtering the input mixed light received from a light emitter 204a via an input window 303a to enable the target light 504a/504b to pass through while blocking the other unwanted light 504b/504a, and a light modulating layer 502a/502b for modulating the target light 504a/504b in a predetermined manner when the light 504a/504b passes through the light modulating layer 502a/502b. In one embodiment, the light emitter 204a and a light detector 204b are arranged on opposite sides of the pulse oximeter, as simply illustrated in FIG. 10A. Under such configuration, the light modulating layer 502a/502b could be a liquid crystal panel 600a or 600b as illustrated by FIG. 6A or 6B. The bottom layer 503a/503b could be omitted and the light 504a/504b passing through and modulated by the liquid crystal panel 600a or 600b will be directly outputted to the output window 303b. In the transmissive mode, the modulation manner of the liquid crystal panel 600a or 600b is opposite to that in the reflective mode. That means, by controlling the electrical field applied to the liquid crystal panel 600a or 600b, the absorption rate or the scattering rate of the input light via the liquid crystal panel 600a or 600b could be varied in a predetermined manner, whereby the intensity of the light signal passing through the liquid crystal panel 600a or 600b could be varied in a predetermined manner, in order to output a modulated light signal having a particular waveform.

Figure 10B:
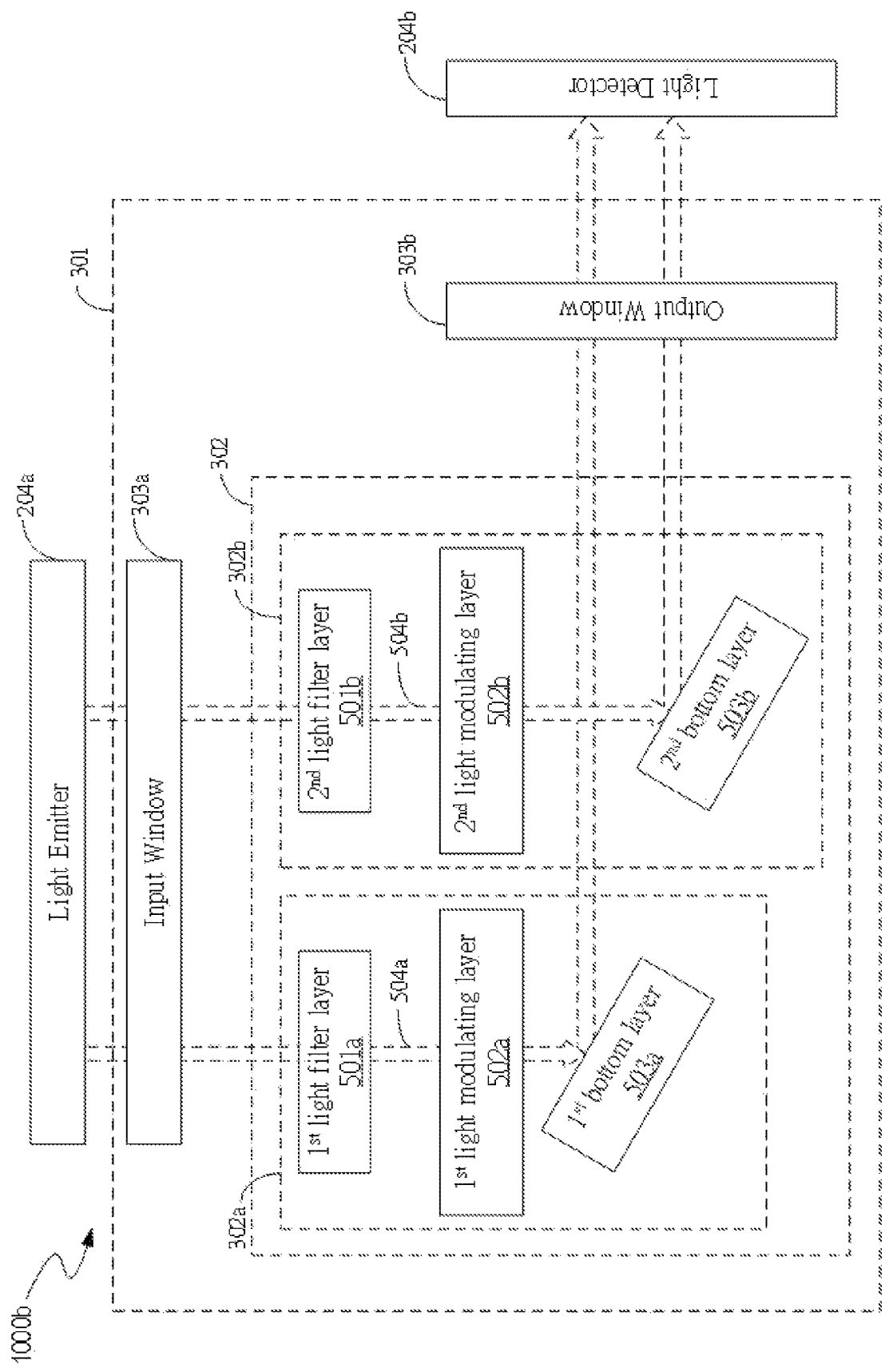
FIG. 10B illustrates a structure of a testing device used for verifying the performance of the non-invasive physiological information detecting device in a transmissive mode, in accordance with another embodiment of the present invention.

In another embodiment, if the light emitter 204a and the light detector 204b are arranged on different sides of the pulse oximeter with an included angle less than 180 degrees there between, as simply illustrated by FIG. 10B, it is needed to change the light transmission direction received from the input window 303a towards the output window 303b. Elements in FIG. 10B with the same or similar reference numerals have the same or similar structure/function as those in previous figures. In one embodiment, if the light modulating layer 502a/502b is a liquid crystal panel 600a or 600b, then the output light signal passed through the light modulating layer 502a/502b will be a modulated light signal. Under such condition, the light modulating unit further includes a bottom layer 503a/503b to change the direction of the modulated light 504a/504b output from the light modulating layer 502a/502b towards the output window 303b. In one embodiment, the bottom layer 503a/503b may be moved to a position between the light filter layer 501a/501b and the light modulating layer 502a/502b to change the light transmission direction towards the output window 303b before the light signal enters the light modulating layer 502a/502b. After that, the light modulating layer 502a/502b is configured at the corresponding light path to modulate the light signal after changing its direction, and directly output the modulated light signal to the output window. Alternatively, the bottom layer 503a/503b could be configured at different positions while satisfying the function of changing the transmission direction of the light towards the output window 303b, no matter before or after the light filter layer 501a/501b and/or light modulating layer 502a/502b. In one embodiment, the bottom layer 703 could be a reflector for reflecting the light towards the output window 303b. In an alternative embodiment, the bottom layer 703 could be a refractor for refracting the light towards the output window 303b. In one embodiment, if the light modulating layer 502a/502b is a digital mirror device 600c as illustrated by FIG. 6C, the bottom layer 503a/503b could be omitted and the controlling unit 611 will control the rotating angle of the mirror 610 to direct varying amounts of light to the output window 303b in a predetermined manner for light modulation.

Figure 10C:
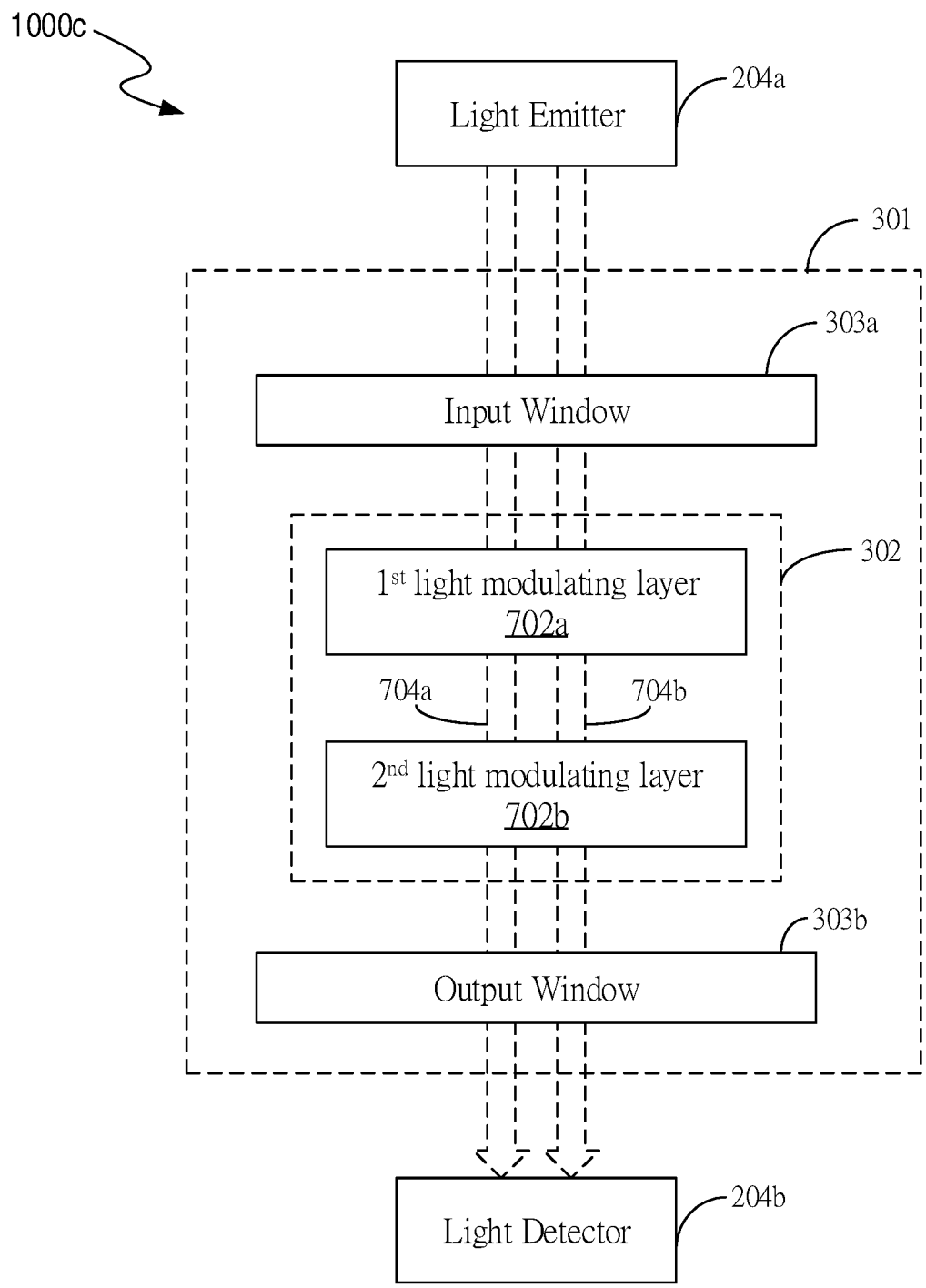
FIG. 10C illustrates a structure of a testing device used for verifying the performance of the non-invasive physiological information detecting device in a transmissive mode, in accordance with another embodiment of the present invention.

FIG. 10C illustrates a structure 1000c of a testing device used for verifying the performance of a non-invasive physiological information detecting device in a transmissive mode, in accordance with one embodiment of the present invention. Elements in FIG. 10C with the same or similar reference numerals have the same or similar structure/function as those in previous figures. FIG. 10C will be described in combination with FIG. 7B. As shown in FIG. 10C, the light modulating unit 302 used for transmissive pulse oximeter has a similar structure as that illustrated in FIG. 7B, wherein at least one of the $1^{st}$ and $2^{nd}$ light modulating layers 702a and 702b will modulate one kind of light when the mixed light passes through it. In one embodiment, one of the $1^{st}$ and $2^{nd}$ light modulating layers 702a and 702b will modulate one kind of light 704a, e.g., the light modulating layer 702a will modulate a red light, and the other one of the 1st and 2nd light modulating layers 702a and 702b will modulate multiple kinds of light 704a and 704b, e.g., the light modulating layer 702b will modulate the red light and an infra-red light. In another embodiment, one of the 1st and 2nd light modulating layers 702a and 702b will modulate one kind of light 704a, e.g., the light modulating layer 702a will modulate a red light, while the other one of the 1st and 2nd light modulating layers 702a and 702b will modulate the other kind of light 704b, e.g., the light modulating layer 702b will modulate an infra-red light. If the light emitter 204a and the light detector 204b are arranged on opposite sides of the pulse oximeter as illustrated in FIG. 10C, the 1st and 2nd light modulating layer 702a or 702b could be a liquid crystal panel 600a or 600b as illustrated in FIGS. 6A or 6B, and the bottom layer 703 will be omitted. During the operation, the light passing through the 2nd light modulating layer 702b will be outputted to the output window 303b directly.

Figure 10D:
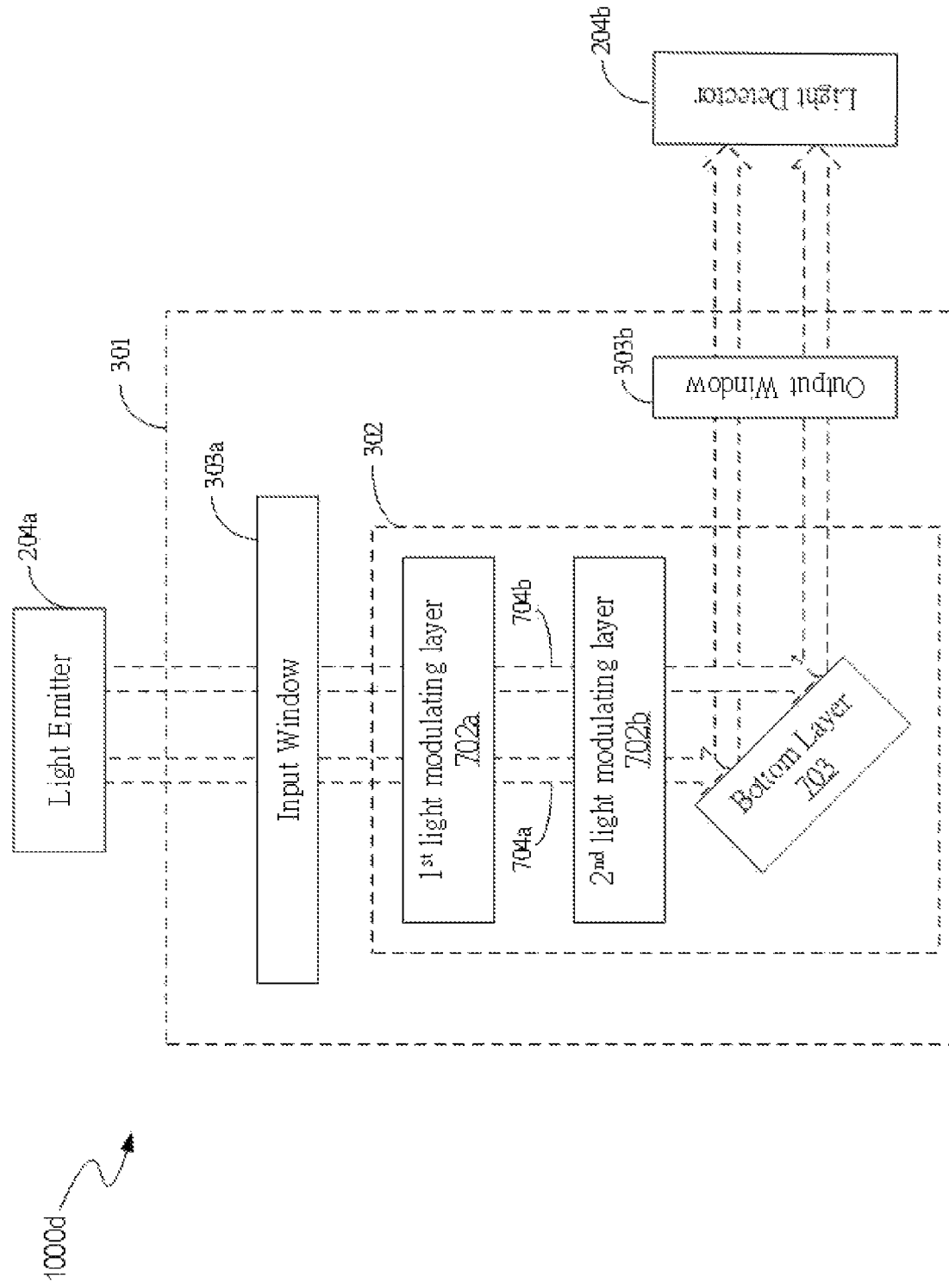
FIG. 10D illustrates a structure of a testing device used for verifying the performance of the non-invasive physiological information detecting device in a transmissive mode, in accordance with another embodiment of the present invention.

In another embodiment, if the light emitter 204a and the light detector 204b are arranged on different sides with an included angle less than 180 degree there between as simply illustrated by FIG. 10D, it is needed to change the light transmission direction received from the input window 303a towards the output window 303b. Elements in FIG. 10D with the same or similar reference numerals have the same or similar structure/function as those in previous figures. In one embodiment, if the light modulating layer 502a/502b is a liquid crystal panel 600a or 600b, then the light modulating unit further includes the bottom layer 703a/703b to re-direct the modulated light 704a/704b to the output window 303b. In one embodiment, the bottom layer 703 may be configured at different positions, e.g., being configured above the 1st light modulating layer 702a or between the 1st and 2nd light modulating layer 702a and 702b, while satisfying the purpose of changing the light transmission direction towards the output window 303b. In one embodiment, the bottom layer 703 could be a reflecting layer for reflecting the light towards the output window 303b. In an alternative embodiment, the bottom layer 703 could be a refracting layer for refracting the light towards the output window 303b. If the 2nd light modulating layer 702b is a digital mirror device 600c as illustrated by FIG. 6C, the bottom layer 703 could be omitted and the controlling unit 611 will control the rotating angle of the mirror 610 to direct varying amount of light to the output window 303b in a predetermined manner for light modulation.

While the foregoing description and the accompanying drawings represent embodiments of the present invention, it will be understood that various additions, modifications and substitutions may be made therein without departing from the spirit and scope of the principles of the present invention as defined in the accompanying claims. One skilled in the art will appreciate that the invention may be used with many modifications of form, structure, arrangement, proportions, materials, elements, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being indicated by the appended claims and their legal equivalents, and not limited to the foregoing description.

What is claimed is:

1. A testing device for verifying performance of a non-invasive physiological information detecting device, comprising:
   a first signal modulating layer being operable for receiving and modulating one or more electromagnetic signals from the physiological information detecting device; and
   a second signal modulating layer for receiving and modulating one or more electromagnetic signals from the first signal modulating layer,
   wherein at least one of the first and second signal modulating layers modulates one electromagnetic signal within the one or more electromagnetic signals according to different target modulating values, wherein the first and second signal modulating layers are selected from a group of a first liquid crystal panel, a second liquid crystal panel and a digital mirror device, wherein the first liquid crystal panel modulates the electromagnetic signals by absorbing the electromagnetic signals in a predetermined manner when the electromagnetic signals passes through it, the second liquid crystal panel modulates the electromagnetic signals by scattering the electromagnetic signals in a predetermined manner, and the digital mirror device modulates the electromagnetic signals by reflecting the electromagnetic signals in a predetermined manner.

2. The testing device of claim 1, wherein the physiological information detecting device emits mixed electromagnetic signals including a first electromagnetic signal with wavelength within a visible light range and a second electromagnetic signal with wavelength within an infra-red light range.

3. The testing device of claim 1, further comprising at least one window for receiving the electromagnetic signals emitted from the physiological information detecting device and outputting the modulated electromagnetic signals to the physiological information detecting device in a substantially reversed direction with respect to a signal emitting direction.

4. The testing device of claim 1, further comprising a bottom layer being operable for processing the electromagnetic signal passing through the second signal modulating layer, such that the modulated signals output to the physiological information detecting device is able to simulate a change of the electromagnetic signal while passing through the blood vessel during the real detecting process.

5. The testing device of claim 4, wherein the first signal modulating layer and the second signal modulating layer modulate the electromagnetic signal based on a target physiological value, the modulated electromagnetic signal is further used for determining the performance of the physiological information detecting device by comparing the physiological value measured by the physiological information detecting device based on the modulated electromagnetic signal with the target physiological value.

6. The testing device of claim 1, further comprising at least two windows positioned at different positions for respectively receiving the electromagnetic signals emitted from the physiological information detecting device and outputting the modulated signals to the physiological information detecting device.

7. The testing device of claim 6, wherein at least one of the first and the second signal modulating layers modulates one kind of electromagnetic signals while let other kind of electromagnetic signals to pass through without modulation.

8. The testing device of claim 6, further comprising a bottom layer for changing a direction of the electromagnetic signals towards the output window.

9. A testing device for verifying performance of a non-invasive physiological information detecting device, comprising:
- a first layer for receiving one or more electromagnetic signals emitted from the physiological information detecting device and modulating at least one of the electromagnetic signals in a first predetermined manner; and
- a second layer for processing and modulating the one or more electromagnetic signals from the first layer such that the modulated signals output to the physiological information detecting device is able to simulate a change of the electromagnetic signals while passing through the blood vessel during the real detecting process, wherein the first predetermined manner is adjustable such that the first layer is able to modulate the one or more electromagnetic signals according to different target modulating values so as to simulate changes of the electromagnetic signals in different real conditions, wherein the first and second layers are selected from a group of a first liquid crystal layer, a second liquid crystal layer and a digital mirror device, wherein the first liquid crystal layer modulates the one or more electromagnetic signals by absorbing the signals in a predetermined manner when the signals passes through it, the second liquid crystal layer modulates the one or more electromagnetic signals by scattering the signals in a predetermined manner when the signals passes through it, and the digital mirror device modulates the one or more electromagnetic signals by reflecting the one or more electromagnetic signals in a predetermined manner.

10. The testing device of claim 9, wherein the second layer modulates the one or more electromagnetic signals received from the first layer in a second predetermined manner.

11. The testing device of claim 9, further comprising a bottom layer for processing the one or more electromagnetic signals passing through the second layer such that the modulated signals received at the blood analysis device is able to simulate the change of the electromagnetic signal while passing through the blood vessel during the real detecting process.

12. The testing device of claim 9, wherein the first layer is a liquid crystal panel being operable for scattering the one or more electromagnetic signals emitted from the physiological information detecting device in the first predetermined manner and the second layer absorbs the one or more electromagnetic signals passing through the first layer.

13. The testing device of claim 12, wherein the first layer scatters different kinds of the electromagnetic signals from the physiological information detecting device with different scattering ratios.

14. The testing device of claim 9, further comprising a mechanical controller that changes a distance between the first layer and the physiological information detecting device and/or an angle between the first layer and the physiological information detecting device for controlling the first layer to modulate the at least one kind of the electromagnetic signals.

15. The testing device of claim 9, wherein a physiological value measured by the physiological information detecting device based on the modulated signal is compared with a target physiological value to determine the performance of the physiological information detecting device.

* * * * *